US008629139B2

(12) United States Patent
Dudley et al.

(10) Patent No.: US 8,629,139 B2
(45) Date of Patent: Jan. 14, 2014

(54) TOPICAL USE OF LEVOFLOXACIN FOR REDUCING LUNG INFLAMMATION

(75) Inventors: Michael N. Dudley, San Diego, CA (US); Ruslan Y. Tsivkovski, San Diego, CA (US); David C. Griffith, San Marcos, CA (US); Olga Rodny, Mountain View, CA (US)

(73) Assignee: MPEX Pharmaceuticals, Inc., Bridgewater, NJ (US)

( * ) Notice: Subject to any disclaimer, the term of this patent is extended or adjusted under 35 U.S.C. 154(b) by 319 days.

(21) Appl. No.: 12/574,666

(22) Filed: Oct. 6, 2009

(65) Prior Publication Data

US 2010/0087386 A1    Apr. 8, 2010

Related U.S. Application Data

(60) Provisional application No. 61/103,496, filed on Oct. 7, 2008.

(51) Int. Cl.
*A61K 31/536* (2006.01)
*C07D 498/14* (2006.01)

(52) U.S. Cl.
CPC ............ *C07D 498/14* (2013.01); *A61K 31/536* (2013.01)
USPC ........................................ 514/230.2; 544/101

(58) Field of Classification Search
None
See application file for complete search history.

(56) References Cited

U.S. PATENT DOCUMENTS

| 2,587,215 A | 2/1952 | Priestly |
| 2,868,691 A | 1/1959 | Porush et al. |
| 3,014,844 A | 12/1961 | Thiel et al. |
| 3,456,644 A | 7/1969 | Thiel |
| 3,456,645 A | 7/1969 | Brock |
| 3,456,646 A | 7/1969 | Phillips et al. |
| 3,507,277 A | 4/1970 | Altounyan et al. |
| 3,565,070 A | 2/1971 | Hanson et al. |
| 3,598,294 A | 8/1971 | Hedrick et al. |
| 3,635,219 A | 1/1972 | Altounyan et al. |
| 3,636,949 A | 1/1972 | Kropp |
| 3,669,113 A | 6/1972 | Altounyan et al. |
| 3,732,864 A | 5/1973 | Thompson et al. |
| 3,789,843 A | 2/1974 | Armstrong et al. |
| 3,807,400 A | 4/1974 | Cocozza |
| 3,826,255 A | 7/1974 | Havstad et al. |
| 3,906,950 A | 9/1975 | Cocozza |
| 3,948,264 A | 4/1976 | Wilke et al. |
| 3,971,377 A | 7/1976 | Damani |
| 3,991,761 A | 11/1976 | Cocozza |
| 4,013,075 A | 3/1977 | Cocozza |
| 4,046,146 A | 9/1977 | Rosskamp et al. |
| 4,147,166 A | 4/1979 | Hansen |
| 4,253,468 A | 3/1981 | Lehmbeck |
| 4,263,907 A | 4/1981 | Lindsey |
| 4,268,460 A | 5/1981 | Boiarski et al. |
| 4,353,365 A | 10/1982 | Hallworth et al. |
| 4,470,412 A | 9/1984 | Nowacki et al. |
| 4,510,929 A | 4/1985 | Bordoni et al. |
| 4,534,345 A | 8/1985 | Wetterlin |
| 4,624,251 A | 11/1986 | Miller |
| 4,648,393 A | 3/1987 | Landis et al. |
| 4,649,911 A | 3/1987 | Knight et al. |
| 4,664,107 A | 5/1987 | Wass |
| 4,667,668 A | 5/1987 | Wetterlin |
| 4,688,218 A | 8/1987 | Blineau et al. |
| 4,730,000 A | 3/1988 | Chu |
| 4,790,305 A | 12/1988 | Zoltan et al. |
| 4,805,811 A | 2/1989 | Wetterlin |
| 4,807,814 A | 2/1989 | Douche et al. |
| 4,809,692 A | 3/1989 | Nowacki et al. |
| 4,811,731 A | 3/1989 | Newell et al. |
| 4,832,015 A | 5/1989 | Nowacki et al. |
| 4,844,902 A | 7/1989 | Grohe |
| 4,857,311 A | 8/1989 | Domb et al. |
| 4,889,144 A | 12/1989 | Tateno et al. |
| 4,907,538 A | 3/1990 | Helmle et al. |
| 4,926,852 A | 5/1990 | Zoltan et al. |
| 4,955,371 A | 9/1990 | Zamba et al. |
| 4,985,557 A | 1/1991 | Hayakawa et al. |
| 5,012,803 A | 5/1991 | Foley et al. |
| 5,012,804 A | 5/1991 | Foley et al. |
| 5,024,467 A | 6/1991 | Truchet |
| 5,027,806 A | 7/1991 | Zoltan et al. |
| 5,033,463 A | 7/1991 | Cocozza |
| 5,040,527 A | 8/1991 | Larson et al. |
| 5,053,407 A | 10/1991 | Hayakawa et al. |

(Continued)

FOREIGN PATENT DOCUMENTS

CN    1312076       9/2002
EP    0 211 595 A2  2/1987

(Continued)

OTHER PUBLICATIONS

Murray, N. "Lung Inflammation Treatment" by eHow Health. [retrieved on Mar. 7, 2013]. Retrieved from the Internet http://www.ehow.com/about_5417681_lung-inflammation-treatment.html.*
Tirouvanziam et al, Am. J. Res. Cell Mol. Biol., 2000, 23, 121-127.*
"Understanding Sarcoidosis" by the American Lung Association. [Retrieved on Mar. 7, 2013]. Retrieved from the Internet http://www.lung.org/lung-disease/sarcoidosis/understanding-sarcoidosis.html.*
"Hypersensitivity Pneumonitis" by the American Lung Association. [Retrieved on Mar. 7, 2013]. Retrieved from the Internet http://www.lung.org/lung-disease/hypersensitivity-pneumonitis/.*
"Cystic Fibrosis," Medline Plus Medical Encyclopedia—accessed at www.nlm.nih.gov/medlineplus/ency/article/000107.htm on Jul. 11, 2008.
"Dynamic, absolute, kinematic viscosity" accessed online at www.engineeringtoolbox.com/dynamic-absolute-kinematicviscosity-d_412.html on Apr. 11, 2011.

(Continued)

*Primary Examiner* — Eric S Olson
(74) *Attorney, Agent, or Firm* — Knobbe, Martens, Olson & Bear, LLP

(57) ABSTRACT

The present invention relates to methods and compositions for the treatment of pulmonary inflammation. In particular, methods and compositions using aerosol levofloxacin or ofloxacin to reduce pulmonary inflammation are provided.

47 Claims, 13 Drawing Sheets

(56) References Cited

U.S. PATENT DOCUMENTS

Figure 1A:
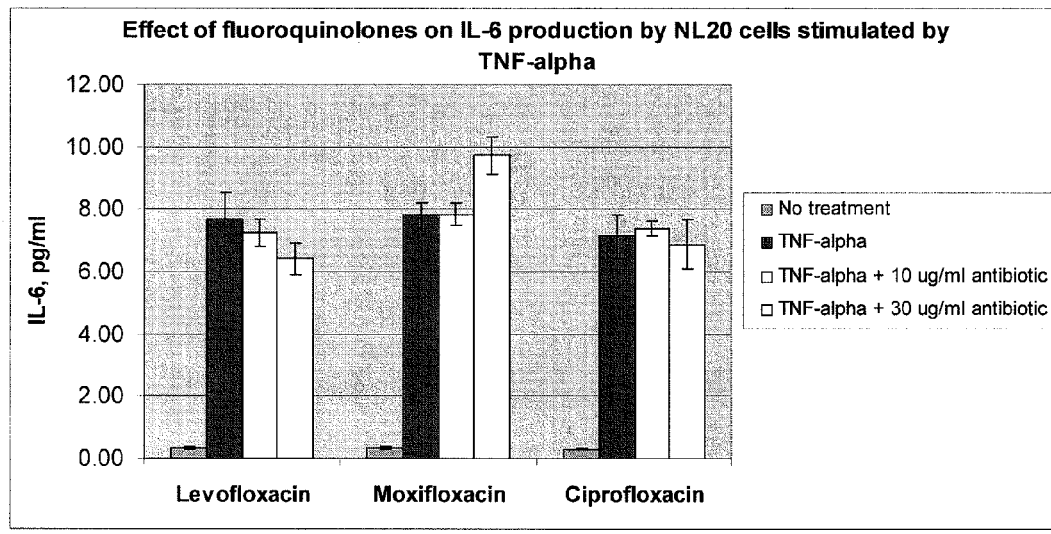

| | | |
|---|---|---|
| 5,060,643 A | 10/1991 | Rich et al. |
| 5,113,855 A | 5/1992 | Newhouse |
| 5,119,806 A | 6/1992 | Palson et al. |
| 5,142,046 A | 8/1992 | Hayakawa et al. |
| 5,164,740 A | 11/1992 | Ivri |
| 5,217,004 A | 6/1993 | Blasnik et al. |
| 5,284,133 A | 2/1994 | Burns et al. |
| 5,304,559 A | 4/1994 | Rozier |
| 5,334,589 A | 8/1994 | Al-Razzak et al. |
| 5,347,998 A | 9/1994 | Hodson et al. |
| 5,364,838 A | 11/1994 | Rubsamen |
| 5,385,140 A | 1/1995 | Smith |
| 5,388,572 A | 2/1995 | Mulhauser et al. |
| 5,404,871 A | 4/1995 | Goodman et al. |
| 5,427,089 A | 6/1995 | Kraemer |
| 5,437,270 A | 8/1995 | Braithwaite |
| 5,478,578 A | 12/1995 | Arnold et al. |
| 5,508,269 A | 4/1996 | Smith et al. |
| 5,549,102 A | 8/1996 | Lintl et al. |
| 5,563,155 A | 10/1996 | Domagala et al. |
| 5,586,550 A | 12/1996 | Ivri et al. |
| 5,642,730 A | 7/1997 | Baran |
| 5,645,049 A | 7/1997 | Foley et al. |
| 5,694,920 A | 12/1997 | Abrams et al. |
| 5,709,202 A | 1/1998 | Lloyd et al. |
| 5,740,794 A | 4/1998 | Smith et al. |
| 5,756,506 A | 5/1998 | Copeland et al. |
| 5,758,637 A | 6/1998 | Ivri et al. |
| 5,775,320 A | 7/1998 | Patton et al. |
| 5,785,049 A | 7/1998 | Smith et al. |
| 5,816,240 A | 10/1998 | Komesaroff |
| 5,820,873 A | 10/1998 | Choi et al. |
| 5,823,179 A | 10/1998 | Grychowski et al. |
| 5,829,434 A | 11/1998 | Ambrosio et al. |
| 5,840,279 A | 11/1998 | Narodylo et al. |
| 5,906,202 A | 5/1999 | Schuster et al. |
| 5,918,594 A | 7/1999 | Asking et al. |
| 5,934,272 A | 8/1999 | Lloyd et al. |
| 5,960,792 A | 10/1999 | Lloyd et al. |
| 5,971,951 A | 10/1999 | Ruskewicz |
| 5,988,160 A | 11/1999 | Foley et al. |
| 6,003,512 A | 12/1999 | Gerde |
| 6,006,747 A | 12/1999 | Eisele et al. |
| 6,026,807 A | 2/2000 | Puderbaugh et al. |
| 6,026,809 A | 2/2000 | Abrams et al. |
| 6,029,662 A | 2/2000 | Marcon |
| 6,070,575 A | 6/2000 | Gonda et al. |
| 6,083,922 A | 7/2000 | Montgomery |
| 6,161,536 A | 12/2000 | Redmon et al. |
| 6,192,876 B1 | 2/2001 | Denyer et al. |
| 6,196,219 B1 | 3/2001 | Hess et al. |
| 6,223,746 B1 | 5/2001 | Jewett et al. |
| 6,230,706 B1 | 5/2001 | Gonda et al. |
| 6,264,922 B1 | 7/2001 | Wood et al. |
| 6,288,080 B1 | 9/2001 | Barsuhn et al. |
| 6,294,178 B1 | 9/2001 | Weinstein et al. |
| 6,333,044 B1 | 12/2001 | Santus et al. |
| 6,333,045 B1 | 12/2001 | Yasueda et al. |
| 6,338,443 B1 | 1/2002 | Piper |
| 6,349,719 B2 | 2/2002 | Gonda |
| 6,350,199 B1 | 2/2002 | Williams et al. |
| 6,367,470 B1 | 4/2002 | Denyer et al. |
| 6,406,880 B1 | 6/2002 | Thornton |
| 6,427,682 B1 | 8/2002 | Klimowicz et al. |
| 6,435,177 B1 | 8/2002 | Schmidt et al. |
| 6,468,967 B1 | 10/2002 | Oleson, Jr. et al. |
| 6,492,328 B2 | 12/2002 | Lehrer et al. |
| 6,503,953 B2 | 1/2003 | Vyden |
| 6,518,239 B1 | 2/2003 | Kuo et al. |
| 6,523,536 B2 | 2/2003 | Fugelsang et al. |
| 6,543,442 B2 | 4/2003 | Gonda et al. |
| 6,544,555 B2 | 4/2003 | Rudnic et al. |
| 6,557,549 B2 | 5/2003 | Schmidt et al. |
| 6,561,186 B2 | 5/2003 | Casper et al. |
| 6,576,224 B1 * | 6/2003 | Osbakken et al. ............ 424/45 |
| 6,579,854 B1 | 6/2003 | Mitchell et al. |
| 6,584,971 B1 | 7/2003 | Denyer et al. |
| 6,585,958 B1 | 7/2003 | Keller et al. |
| 6,586,008 B1 | 7/2003 | Batycky et al. |
| 6,601,581 B1 | 8/2003 | Babaev |
| 6,605,609 B2 | 8/2003 | Barbachyn et al. |
| 6,608,078 B2 | 8/2003 | De Souza et al. |
| 6,612,303 B1 | 9/2003 | Grychowski et al. |
| 6,626,173 B2 | 9/2003 | Genova et al. |
| 6,644,304 B2 | 11/2003 | Grychowski et al. |
| 6,663,890 B2 | 12/2003 | Rudnic et al. |
| 6,663,891 B2 | 12/2003 | Rudnic et al. |
| 6,664,239 B2 | 12/2003 | Mitchell et al. |
| 6,667,042 B2 | 12/2003 | Rudnic et al. |
| 6,667,057 B2 | 12/2003 | Rudnic et al. |
| 6,669,948 B2 | 12/2003 | Rudnic et al. |
| 6,672,304 B1 | 1/2004 | Casper et al. |
| 6,681,768 B2 | 1/2004 | Haaije de Boer et al. |
| 6,689,769 B2 | 2/2004 | Gordeev et al. |
| 6,716,819 B2 | 4/2004 | Welsh et al. |
| 6,723,341 B2 | 4/2004 | Rudnic et al. |
| 6,730,320 B2 | 5/2004 | Rudnic et al. |
| 6,756,369 B2 | 6/2004 | Mitchell et al. |
| 6,806,256 B2 | 10/2004 | Ulrich et al. |
| 6,835,372 B2 | 12/2004 | Kuo et al. |
| 6,838,552 B1 | 1/2005 | Mitchell et al. |
| 6,869,965 B2 | 3/2005 | Gordeev et al. |
| 6,878,713 B2 | 4/2005 | De Souza et al. |
| 6,884,784 B1 | 4/2005 | Mitchell et al. |
| 6,890,526 B2 | 5/2005 | Stratton et al. |
| 6,962,151 B1 | 11/2005 | Knoch et al. |
| 6,987,094 B2 | 1/2006 | Malvolti et al. |
| 7,148,404 B2 | 12/2006 | Hogenhaug et al. |
| 7,838,532 B2 | 11/2010 | Surber et al. |
| 2001/0049366 A1 | 12/2001 | Singh et al. |
| 2002/0061281 A1 | 5/2002 | Osbakken et al. |
| 2002/0086867 A1 | 7/2002 | Dubois et al. |
| 2002/0142050 A1 | 10/2002 | Straub et al. |
| 2002/0197212 A1 | 12/2002 | Osbakken et al. |
| 2003/0012814 A1 | 1/2003 | Rudnic et al. |
| 2003/0028025 A1 | 2/2003 | Raghavan |
| 2003/0032600 A1 | 2/2003 | Ulrich et al. |
| 2003/0078517 A1 | 4/2003 | Kensey |
| 2003/0138403 A1 | 7/2003 | Drustrup |
| 2003/0171340 A1 | 9/2003 | Isbister |
| 2003/0186894 A1 | 10/2003 | Kuo et al. |
| 2004/0009126 A1 | 1/2004 | Pilkiewicz et al. |
| 2004/0009989 A1 | 1/2004 | Niddam-Hildesheim et al. |
| 2004/0014750 A1 | 1/2004 | Michaelis et al. |
| 2004/0045546 A1 | 3/2004 | Hirsh et al. |
| 2004/0152701 A1 | 8/2004 | Reddy et al. |
| 2005/0036951 A1 | 2/2005 | Henderson |
| 2005/0106151 A1 | 5/2005 | Shapiro |
| 2005/0139211 A1 | 6/2005 | Alston et al. |
| 2005/0147567 A1 | 7/2005 | Kuo et al. |
| 2005/0235987 A1 | 10/2005 | Smaldone et al. |
| 2005/0260099 A1 | 11/2005 | Xia et al. |
| 2005/0288302 A1 | 12/2005 | Niddam-Hildesheim et al. |
| 2006/0003944 A1 | 1/2006 | Glinka et al. |
| 2006/0025355 A1 | 2/2006 | Duddu et al. |
| 2006/0223751 A1 | 10/2006 | Mygind et al. |
| 2006/0258677 A1 | 11/2006 | Amir et al. |
| 2006/0276416 A1 | 12/2006 | Sinclair et al. |
| 2006/0276463 A1 | 12/2006 | Sharma et al. |
| 2006/0276473 A1 | 12/2006 | Bostion et al. |
| 2006/0276483 A1 | 12/2006 | Surber et al. |
| 2006/0286574 A1 | 12/2006 | Romesberg et al. |
| 2007/0003753 A1 | 1/2007 | Asgari |
| 2007/0071686 A1 | 3/2007 | Lintz et al. |
| 2007/0155715 A1 | 7/2007 | van Duzer et al. |
| 2007/0197548 A1 | 8/2007 | Murthy |
| 2009/0025713 A1 | 1/2009 | Keller et al. |
| 2010/0087416 A1 | 4/2010 | Griffith et al. |
| 2010/0204470 A1 | 8/2010 | Wieser et al. |

FOREIGN PATENT DOCUMENTS

| | | |
|---|---|---|
| EP | 0 347 779 | 12/1989 |
| EP | 0 455 463 A1 | 11/1991 |

(56) References Cited

FOREIGN PATENT DOCUMENTS

| | | |
|---|---|---|
| EP | 0 467 172 A1 | 1/1992 |
| EP | 0 470 667 A1 | 2/1992 |
| EP | 0 855 183 A2 | 7/1998 |
| EP | 1 092 430 A1 | 4/2001 |
| EP | 1 223 915 B1 | 12/2005 |
| GB | 901107 A | 7/1962 |
| SU | 628930 | 10/1978 |
| WO | WO 87/05213 | 9/1987 |
| WO | WO 90/07351 | 7/1990 |
| WO | WO 90/13327 | 11/1990 |
| WO | WO 92/09322 | 6/1992 |
| WO | WO 93/12831 | 7/1993 |
| WO | WO 93/24165 | 12/1993 |
| WO | WO 95/11666 | 5/1995 |
| WO | WO 96/23485 | 8/1996 |
| WO | WO 97/03649 | 2/1997 |
| WO | WO 98/03217 | 1/1998 |
| WO | WO 99/59566 | 11/1999 |
| WO | WO 99/62495 | 12/1999 |
| WO | WO 00/18388 A1 | 4/2000 |
| WO | WO 01/02024 | 1/2001 |
| WO | WO 02/18345 | 3/2002 |
| WO | WO 02/072102 | 9/2002 |
| WO | WO 03/035030 A1 | 5/2003 |
| WO | WO 03/066064 A2 | 8/2003 |
| WO | WO 03/075889 A1 | 9/2003 |
| WO | WO 2004/019912 | 3/2004 |
| WO | WO 2005/037256 A2 | 4/2005 |
| WO | WO 2005/089738 | 9/2005 |
| WO | WO 2006/011051 A1 | 2/2006 |
| WO | WO 2006/033713 | 3/2006 |
| WO | WO 2006/078925 A2 | 7/2006 |
| WO | WO 2006/125132 A2 | 11/2006 |
| WO | WO 2007/085057 | 8/2007 |
| WO | WO 2007/090123 | 8/2007 |
| WO | WO 2007/090646 | 8/2007 |
| WO | WO 2007/095156 | 8/2007 |
| WO | WO 2007/095187 | 8/2007 |
| WO | WO 2008/025560 A1 | 3/2008 |
| WO | WO 2009/140587 | 11/2009 |
| WO | WO 2010/042549 | 4/2010 |
| WO | WO 2010/042553 | 4/2010 |
| WO | WO 2010/124141 | 10/2010 |
| WO | WO 2011/022075 | 2/2011 |
| WO | WO 2011/029059 | 3/2011 |

OTHER PUBLICATIONS

Seddon, "Pseudopolymorph: a polemic", Crystal Growth & Design (2004) 4(6):1087, web release date Oct. 19, 2004.
"Surface Tension," The Engineering Toolbox—accessed at www.engineeringtoolbox.com/surface-tensiond_962.html on Jun. 21, 2011.
Vippagunta et al., "Crystalline Solids", Adv Drug Deliv Rev. (2001) 48(1):3-26.
Abusriwil et al. "The interaction of host and pathogen factors in chronic obstructive pulmonary disease exacerbations and their role in tissue damage", Proc. Am. Thorac. Soc. (2007) 4(8):611-617.
Aggarwal et al., "Predictors of mortality and resource utilization in cirrhotic patients admitted to the medical ICU", Chest (2001) 119(5):1489-1497.
Ambrose, Paul G.et al., "Pharmacokinetics-Pharmacodynamics of Antimicrobial Therapy: It's Not Just for Mice Anymore", Antimicrobial Resistance (2007) 44:79-86.
Amsden, "Anti-inflmmatory effects of macrolides-an underappreciated benefit in the treatment of community-acquired respiratory tract infections and chronic inflammatory pulmonary conditions?", Journal of Antimicrobial Chemotherapy (2005) 55:10-21.
Anonymous, "MPEX Pharmaceuticals Initiates Multi-Dose Clinical Trial in the U.S. with MP-376 in Patients with Cystic Fibrosis" Science Letter (2007) 2 pages.
Anonymous, Mpex Candidate, MP-376, Granted US Orphan Drug Status for the Treatment of Cystic Fibrosis, Medical News Today, www.medicalnewstoday.com (retrieved online Dec. 11, 2009), Mar. 5, 2008, XP002560239.

Araujo et al., "Effect of moxifloxacin on secretion of cytokines by human monocytes stimulated with lipopolysaccharide", Clin. Microbiol. Infect. (2002) 8:26-30.
Araujo et al., "Gemifloxacin inhibits cytokine secretion by lipopolysaccharide stimulated human monocytes at the post-transcriptional level", Clin. Microbiol. Infect. (2004) 10:213-219.
Arzte, Zeitung DE, www.aerztezeitung.de/extras/druckansicht/?sid=347342&pid=351267 (retrieved online Dec. 11, 2009), Mar. 14, 2005, XP002560241. (Machine Translation Provided).
Atkins et al., "The Design and Development of Inhalation Drug Delivery Systems", Pharmaceutical Inhalation Aerosol Technology, Marcel Dekker, Inc., New York, NY (1992) 6: p. 155-185.
Baker et al., "A Prodrug Approach Toward the Development of Water Soluble Fluoroquinolones and Structure-Activity Relationships of Quinoline-3-Carboxylic Acids" J. Med. Chem. (2004) 47:4693-4709.
Banerjee et al., "The treatment of respiratory pseudomonas infection in cystic fibrosis: what drug and which way?" Drugs (2000) 60(5):1053-64. (Abstract Only).
Barry et al., "Novel agents in the management of Mycobacterium tuberculosis disease" Current medicinal chemistry (Netherlands) (2007) 14(18):2000-8. (Abstract Only).
Battram et al., "In vitro and in vivo pharmacological characterization of 540-[® -2-(5,6-diethyl-idan-2-ylamino)-1-hydroxy-ethyl]-8-hydroxy-1H-quinolin-2-one (indacterol), a novel inhaled beta(2) adrenoceptor agonist with a 24-h duration of action", J Pharmacol Exp Ther. (2006) 317(2):762-70. (Abstract Only).
Beasley et al., "Adverse reactions to the non-drug constituents of nebuliser solutions", Br. J. clin. Pharmac., (1988) 25: p. 283-287.
Benko et al., "Pharmacokinetics and pharmacodynamics of levofloxacin in critically ill patients with ventilator-associated pneumonia" International journal of antimicrobial agents (Netherlands) (2007) 30(2):162-8. (Abstract Only).
Berg, "Combination products are spotlighted at Drug/Device Summit" The BBI Newsletter (2005). (Abstract Only).
Blaser et al., "Influence of Medium and Method on the in Vitro Susceptibility of Pseudomonas Aeruginos and Other Bacteria to Ciprofloxacin and Enoxacin, Antimicrobial Agents and Chemotherapy", American Society for Microbiology (1986) 29(5):927-929.
Blau et al., "Moxifloxacin but not Ciprofloxacin or Azithromycin Selectively Inhibits IL-8, IL-6, ERK1/2, JNK, and NF-κB Activation in a Cystic Fibrosis Epithelial Cell Line", Am. J. Physiol. Lung Cell Mol. Physiol. (2007) 292:L343-L352.
Blitz et al., "Aerosolized Magnesium Sulfate for Acute Asthma: A Systematic Review", Chest the Cardiopulmonary and Critical Care Journal, (2005) 128: p. 337-344.
Brouillard et al., "Antibiotic selection and resistance issues with fluoroquinolones and doxycycline against bioterrorism agents" Pharmacotherapy (United States) (2006) 26(1):3-14. (Abstract Only).
Bryskier, "*Bacillus anthracis* and antibacterial agents" Clinical microbiology and infection—the official publication of the European Society of Clinical Microbiology and Infectious Diseases (France) (2002) 8(8):467-78. (Abstract Only).
Calbo et al., "Systemic expression of cytokine production in patients with severe pneumococcal pneumonia: effects of treatment with a beta-lactam versus a fluoroquinolone, antimicrobial agents and chemotherapy", American Society for Microbiology (2008) 52(7):2395-2402.
Carratala et al., "Clinical experience in the management of community-acquired pneumonia: lessons from the use of fluoroquinolones" Clinical microbiology and infection—the official publication of the European Society of Clinical Microbiology and Infectious Diseases (France) (2006) 12(3):2-11. (Abstract Only).
Cazzola, et al., "Delivering antibacterials to the lungs: considerations for optimizing outcomes", Am. J. Respir. Med. (2002) 1(4):261-272.
Celli et al., "The body-mass index, airflow obstruction, dyspnea, and exercise capacity index in chronic obstructive pulmonary disease", N Engl J Med. (2004) 350(10):1005-1012.
Chang et al., Properties of the Drug Molecule in Nasal Systemic Drug Delivery, 1989, pp. 49-51, Chapter 3, Marcel Dekker, Inc.
Chhabra et al. "Evaluation of three scales of dyspnea in chronic obstructive pulmonary disease" Ann Thorac Med (2009) 4:128-132.

(56) References Cited

OTHER PUBLICATIONS

Chien et al., "Properties of the Drug Molecule in Nasal Systemic Drug Delivery", (1989) pp. 63-68, Chapter 3, Marcel Dekker, Inc.

Chodosh S., "Clinical significance of the infection-free interval in the management of acute bacterial exacerbations of chronic bronchitis", Chest (2005) 127(6):2231-2236.

Choi et al., "Effect of moxifloxacin on production of proinflammatory cytokines from human peripheral blood mononuclear cells", Antimicrobial Agents and Chemotherapy (2003) 47(12):3704-3707.

Cigana et al., "Azithromycin selectively reduces tumor necrosis factor alpha levels in cystic fibrosis airway epithelial cells", Antimicrob. Agents Chemother. (2007) 51(3):975-981.

Conrad, "Mpex 204 Phase 2", Stanford School of Medicine (retrieved online Dec. 11, 2009), Sep. 3, 2008, pp. 1-7 (PCT ISR/WO provided a partial reference, and the full reference is no longer available.).

Conte et al., "intrapulmonary pharmacodynamics of high-dose levofloxacin in subjects with chronic bronchitis or chronic obstructive pulmonary disease", International Journal of Antimicrobial Agents, Elsevier Science, Amsterdam, NL (2007) 30(5):422-427.

Cooney et al., "Absolute bioavailability and absorption characteristics of aerosolized tobramycin in adults with cystic fibrosis", J. Clinical Pharmacol. (1994) 34(3):255-259.

Dalhoff et al., "Immunomodulatory effects of quinolones",The Lancet Infectious Diseases (2003) 3:359-71.

Dalhoff, "Immunomodulatory activities of fluoroquinolones", Infection (2005) 33(Suppl 2):55-70.

Den Hollander, et al., "Synergism between tobramycin and ceftazidime against a resistant *Pseudomonas aeruginosa* strain, tested in an in vitro pharmacokinetic model", Antimicrob. Agents Chemother. (1997) 41(1):95-100.

DeRyke et al., "Pharmacodynamic target attainment of six beta-lactams and two fluoroquinolones against *Pseudomonas aeruginosa*, *Acinetobacter baumannii*, *Escherichia coli*, and *Klebsiella* species collected from United States intensive care units in 2004" Pharmacotherapy (United States) (2007) 27(3):333-42. (Abstract Only).

Diakov et al., "The chemotherapeutic efficacy of ciprofloxacin and lomefloxacin in the inhalation method of infecting white mice with tularemia., Khimioterapevticheskaia effektivnost' tsiprofloksatsina i lomefloksatsina pri ingaliatsionnom sposbe zarazheniia tuliaremiei belykh myshei" Antibiotiki i khimioterapii a = Antibiotics and chemotherapy sic / Ministerstvo miditsinskoi i mikrobiologicheskoi promyshelennnosti SSSR (Russia) (2000) 45(6):17-20. (Abstract Only).

Donnarumma et al., "Anti-inflammatory effects of moxifloxacin and human beta-defensin 2 association in human lung epithelial cell line (A549) stimulated with lipopolysaccharide", Peptides (2007) 28:2286-2292.

Doring et al., "Antibiotic therapy against *Pseudomonas aeruginosa* in cystic fibrosis: a European consensus" [comment in Eur Respir J. 2000 16(4):585-7], Euro Respir J. (2000) 16(4):749-67. (Abstract Only).

Drevensek et al., "Influence of Copper(II) and Magnesium(II) ions on the Ciprofloxacin Binding to DNA", J.Inorg. Biochem. (2003) 96:407-415.

Drevensek et al., "X-Ray Crystallographic, NMR and Antimicrobial Activity Studies of Magnesium Complexes of Fluoroquinolones—Racemic Ofloxacin and its S-form, Levofloxacin" J. Inorg. Biochem. (2006) 100:1755-1763.

Drusano et al., "Pharmacodynamics of a Fluoroquinolone Antimicrobial Agent in a Neutropenic Rat Model of *Pseudomonas* Sepsis" Antimicrob. Agents & Chemother. (1993) 37(3):483-490.

Elizur et al., "Airway inflammation in cystic fibrosis," Chest (2008) 133:489-495.

File, "A New Dosing Paradigm: High-Dose, Short-Course Fluoroquinolone Therapy for Community-Acquired Pneumonia" Clinical Cornerstone (2003) 3:S21-S28.

Flume et al., "Cystic Fibrosis Pulmonary Guidelines: Chronic Medications for Maintenance of Lung Health," Am J Respir Crit Care Med (2007) 176:957-969.

Fuchs et al., "Effect of aerosolized recombinant human DNase on exacerbations of respiratory symptoms and on pulmonary function in patients with cystic fibrosis", The Pulmozyme Study Group, N Engl J Med. (1994) 331(10):637-642.

Garrity et al., "Bergey's Manual of Systematic Bacteriology," Editor-in-chief: Garrity, George M. Boone, David R.; Castenholz, Richard W. (Eds.) Originally published by Williams & Wilkins, 1984, 2nd ed. (2001).

Gavilanes et al., "Azithromycin fails to reduce increased expression of neutrophil-related cytokines in primary-cultured epithelial cells from cystic fibrosis mice", J. Cyst. Fibros. (2009) 10(1016):1-8.

Goh et al., "Current Status of Topical Nasal Antimicrobial Agents" The Laryngoscope (2000) 110:875-880.

Griese et al., "Amphotericin B and Pulmonary Surfactant", European Journal of Medical Research, I. Holzapfel Publishers (1998) 3:383-386.

Griffith et al., "Pharmacodynamics of levofloxacin against *Pseudomonas aeruginosa* with reduced susceptibility due to different efflux pumps: do elevated MICs always predict reduced in vivo efficacy?" Antimicrob Agents Chemother. (2006) 50(5):1628-32.

Griffith et al., "Efficacy of fluoroquinolones against *Leptospira interrogans* in a hamster model" Antimicrobial agents and chemotherapy (United States) (2007) 51(7):2615-7. (Abstract only).

Griffith et al., In-vitro antibacterial activity of aerosol MP 376 in mouse models of pulmonary infection, Pediatr. Pulmonol. (2007) 42(S30):304.

Griffith et al., "Pharmacokinetics and Safety of MP-376 (Levofloxacin Solution for Inhalation) in Normal Healthy Volunteers and Cystic Fibrosis Patients", Pediatr. Pulmonol., (2007) 42(S30):303.

Guina et al., "Quantitative proteomic analysis indicates increased synthesis of a quinolone by *Pseudomonas aeruginosa* isolates from cystic fibrosis airways", PNAS, Mar. 4, 2003, vol. 100, No. 5, p. 2771-2776.

Hart et al., "Cross-over assessment of serum bactericidal activity of moxifloxacin and levofloxacin versus penicillin-susceptible and penicillin-resistant *Streptococcus pneumoniae* in healthy volunteers", Diagnostic microbiology and infectious disease (United States) (2007) 58(3):375-8. (Abstract Only).

Hashimoto et al., "Grepafloxacin Inhibits Tumor Necrosis Factor-alpha-induced Interleukin-8 Expression in Human Airway Epithelial Cells", Life Sci (2000) 66(5):PL 77-82.

Hecht et al., "In vitro activities of 15 antimicrobial agents against 110 toxigenic clostridium difficile clinical isolates collected from 1983 to 2004" Antimicrobial agents and chemotherapy (United States) (2007) 51(8):2716-9. (Abstract Only).

Heine et al., "Comparison of 2 antibiotics that inhibit protein synthesis for the treatment of infection with yersinia pestis delivered by aerosol in a mouse model of pneumonic plague", Journal of Infectious Diseases (United States) (2007) 196(5):782-7. (Abstract Only).
Hodson, "Antibiotic Treatment: Aerosol Therapy", Chest (1988) 94:156S-160S.
Hoffmann, et al., "Novel mouse model of chronic *Pseudomonas aeruginosa* lung infection mimicking cystic fibrosis", Infect. Immun. (2005) 73(4):2504-2514.
Honey Bourne, "Antibiotic penetration in the respiratory tract and implications for the selection of antimicrobial therapy" Curr Opin Pulm Med. (1997) 3(2):170-4. (Abstract Only).
Horiguchi et al., "Usefulness of sparfloxacin against *Chlamydia pneumoniae* infection in patients with bronchial asthma" Journal of international medical research (England) Nov.-Dec. 2005 33(6):668-76. (Abstract Only).
Hrkach et al., "Synthesis of poly(I-lactic acid-co-L-lysine) graft copolymers", Macromolecules (1995) 28: 4736-4739.
Huang et al., "Oxidation of fluoroquinolone antibacterials and structurally related amines with manganese oxide" National Meeting—American Chemical Society Division of Environmental Chemistry (2003) 43(2)(5):1257-1260.

(56) References Cited

OTHER PUBLICATIONS

Hung et al., "Evaluation of two commercial jet nebulisers and three compressors for the nebulisation of antibiotics", Archives of Disease in Childhood (1994) 71(4):335-338.
Hutschala et al., "In vivo measurement of levofloxacin penetration into lung tissue: CPB versus OPCAB" European Journal of Anaesthesiology (2005) 49(12) 5107-11.
Jacquot et al., "Airway epithelial cell inflammatory signalling in cystic fibrosis," The International Journal of Biochemistry & Cell Biology (2008) 40:1703-15.
Jarraud et al., "Legionnaires disease (Legionellose)" Presse medicale (Paris, France—1983) (France) (2007) 36(2 Pt 2):279-87. (Abstract Only).
Jensen et al., "The efficacy and safety of ciprofloxacin and ofloxacin in chronic Pseudomonas aeruginosa infection in cystic fibrosis", J Antimicrob Chemother. (1987) 20(4):585-94.
Jones et al., "Quantifying of severity of exacerbations in chronic obstructive pulmonary disease: adaptations to the definition to allow quantification", Proc Am Thorac Soc. (2007) 4(8):597-601.
Jumbe et al., "Application of a mathematical model to prevent in vivo amplification of antibiotic-resistant bacterial populations during therapy", J Clin Invest. (2003) 112(2):275-85.
Khan et al., "Effect of trovafloxacin on production of cytokines by human monocytes", Antimicrobial Agents and Chemotherapy (1998) 42(7):1713-7.
Khan et al., "Protection against lipopolysaccharide-induced death by fluoroquinolones," Antimicrobial Agents and Chemotherapy, (2000) 44(11): 3169-73.
King et al., "Effect of oxygen limitation on the in vitro activity of levofloxacin and other antibiotics administered by the aerosol route against Pseudomonas aeruginosa from cystic fibrosis patients", Diagn Microbiol Infect Dis. Feb. 2010;66(2):181-6. Epub Oct. 13, 2009.
Kitazawa et al., "Biphasic regulation of levofloxacin on lipopolysaccharide-induced IL-1B production", Life Sciences, (2007) 80:1572-1577.
Kobayashi et al., "Antibacterial activity of tosufloxacin against major organisms detected from patients with respiratory infections" Japanese journal of antibiotics (Japan) (2007) 60(2):98-106. (Abstract Only).
Kohyama et al., "Fourteen-member macrolides inhibit interleukin-8 release by human eosinophils from atopic donors", Antimicrobial Agents and Chemotherapy (1999) 43(4):907-911.
Kraynack et al., "Improving care at cystic fibrosis centers through quality improvement", Semin Respir Crit Care Med. (2009) 30(5):547-558.
Kuhn, "Formulation of aerosolized therapeutics", Chest, The Cardiopulmonary and Critical Care Journal (2001) 120(3):94S-98S. (Abstract Only).
Kurosaka et al., "DX-619, a novel des-F(6)-quinolone: pharmacodynamics (PD) activity and thereapeutic efficacy in animal infection models", Interscience Conference on Antimicrobial Agents and Chemotherapy (2003) 43rd: Chicago.
LaPlante et al., "Fluoroquinolone resistance in *Streptococcus pneumoniae*: area under the concentration-time curve/MIC ratio and resistance development with gatifloxacin, gemifloxacin, levofloxacin, and moxifloxacin" Antimicrobial agents and chemotherapy (United States) (2007) 51(4):1315-20. (Abstract Only).
Le Conte et al., "Lung Distribution and Pharmacokinetics of Aerosolized Tobramycin", American Review of Respiratory Disease, (1993) vol. 147, p. 1279-1282.
Lee et al., "Levofloxacin pharmacokinetics in adult cystic fibrosis", Chest (2007) 131(3):796-802.
Legssyer et al., "Azithromycin reduces spontaneous and induced inflammation in F508 cystic fibrosis mice", Respiratory Research (2006) 7(134):1-13.
Leiva et al., "Effects of telithromycin in in vitro and in vivo models of lipopolysaccharide-induced airway inflammation", Chest (2008) 134:20-29.
Leonard et al., "Topical Antibiotic Therapy for Recalcitrant Sinusitis" The Laryngoscope (1999) 109(4): 668-670.
Lode et al., "Levofloxacin versus clarithromycin in copd exacerbation: focus on exacerbation-free interval", Eur Respir J. (2004) 24(6):947-953.
Louie et al., "Impact of resistance selection and mutant growth fitness on the relative efficacies of streptomycin and levofloxacin for plague therapy", Antimicrob Agents Chemother. (2007) 51(8):26612667. Epub May 21, 2007. (Abstract Only).
Martinez et al., "Appropriate outpatient treatment of acute bacterial exacerbations of chronic bronchitis", American Journal of Medicine, Elsevier Science, Amsterdam, NL (2005) 118(7A): 39S-44S.
Matthys, "Inhalation delivery of asthma drugs" Lung. (1990) 168:645-52. (Abstract Only).
Meguro et al., "Development and validation of an improved, COPD-specific version of the St George's Respiratory Questionnaire" Chest (2007) 132(2):456-463.
Miller et al., "Standardisation of spirometry", American Thoracic Society/European Respiratory Society (ATS/ERS) Spirometry Standards, Eur Respir J (2005) 26(2):319-338.
Mohammed et al., "Intravenous and nebulised magnesium sulphate for acute asthma: systematic review and meta-analysis", Emergency Medicine Journal (2007) 24: p. 823-830.
Moss, "Administration of aerosolized antibiotics in cystic fibrosis patients" Chest (2001) 120(3):107S-113S. (Abstract Only).
Murphy et al., "*Pseudomonas aeruginosa* in chronic obstructive pulmonary disease", Am J Respir Crit Care Med. (2008) 177(8):853-60. Epub Jan. 17, 2008.
Nakanishi et al., "A case of cystic fibrosis in a Japanese student" Nihon Kyobu Shikkan Gakkai zasshi (Japan) (1995) 33(7):771-4. (Abstract Only).
Neu, "The Effects of Cations Upon the Activity of Quinolone Agents", Quinolones Bulletin, Reports on Gyrase Inhibitors (1985).
Neu et al., "In Vitro Activity of 5-Ofloxacin", Antimicrobial Agents and Chemotherapy, American Society for Microbiology (1989) 33 (7):1105-1107.
Newman, "Aerosols and the Lung:Clinical and Experimental Aspects", Butterworth & Co. Ltd., London, England (1984) 197-224.
Nouira et al., "Once daily oral ofloxacin in chronic obstructive pulmonary disease exacerbation requiring mechanical ventilation: a randomised placebo-controlled trial", Lancet (North American Edition) (2001) 358(9298): 2020-2025.
O-Lee et al, "Fluoroquinolone-induced arthralgia and myalgia in the treatment of sinusitis", Am. J. Rhinol. (2005) 19(4):395-399.
Ono et al., "Effect of grepafloxacin on cytokine production in vitro", Journal of Antimicrobial Chemotherapy, (2000) 46:91-94.
Ortho-Mcneil Pharmaceutical, Inc., OMP Division, Text of Proposed Labeling for Levaquin® (2004) 1-52.
Ortho-McNeil Pharmaceutical, Inc., Package Insert for Levaquin®, (2006) 15 pages.
Palmer et al., "Membrane-bound nitrate reductase is required for anaerobic growth in cystic fibrosis sputum", J Bacteriol. (2007) 189(12):4449-55. Epub Mar. 30, 2007.
Pellegrino et al., "Interpretative strategies for lung function tests", Eur Respir J. (2005) 26(5):948-968.
Perez et al., "CFTR inhibition mimics the cystic fibrosis inflammatory profile", Am J. Physiol. Lung Cell Mol Physiol, (2007) 292(2):L383-395. Epub Aug. 18, 2006.
"Physician's Desk Reference", 52.sup.nd ed., Medical Economics, Montvale, N.J. (1998).
Preston et al., "Pharmacodynamics of levofloxacin: a new paradigm for early clinical trials," JAMA. (1998) 279(2):125-129.
Querol-Ribelles et al., "Discrepancy between antibiotics administered in acute exacerbations of chronic bronchitis and susceptibility of isolated pathogens in respiratory samples: multicentre study in the primary care setting" International journal of antimicrobial agents (Netherlands) (2006) 28(5):472-6. (Abstract Only).
Ratcliffe et al., "Effects of Magnesium on the Activity of 4-Quinolone Antibacterial Agents", Journal of Pharmacy and Pharmacology, 1983, p. 61, vol. 35, Supplement Dec. 1983, The Pharmaceutical Society of Great Britain.

(56) References Cited

OTHER PUBLICATIONS

Reato et al., "Immunomodulating effect on antimicrobial agents on cytokine production by human polymorphonuclear neutrophils", International Journal of Antimicrobial Agents (2004) 23:150-154.
Rennard, "COPD: overview of definitions, epidemiology, and factors influencing its development", Chest (1998) 113 (Suppl 4):235-41s).
Romano et al., "[the use of ofloxacin in cystic fibrosis patients.] Uso dell'ofloxacin nei pazienti con fibrosi cistica", Minerva Pediatr. (1992) 44(3):79-86. (Abstract Only).
Rosell et al., 2005. Microbiologic determinants of exacerbation in chronic obstructive pulmonary disease. Arch Intern Med 165: 891-897.
Rosenfeld et al., "Defining a pulmonary exacerbation in cystic fibrosis ", J Pediatr. (2001) 139(3):359-365.
Ross et al., Physicochemical properties of the fluoroquinolone antimicrobials V. effect of fluoroquinolone structure and pH on the complexation of various fluoroquinolones with magnesium and calcium ions, International Journal of Pharmaceutics (1993) 93:121-129.
Sabet et al., "Efficacy of Aerosol MP-376, a levofloxacin inhalation solution, in models of mouse lung infection due to *Pseudomonas aeruginosa*, Antimicrobial Agents and Chemotherapy", (2009) 53(9):3923-3928.
Sabet et al., "In-Vivo Antibacterial Activity of Aerosol MP-376 in Mouse Models of Pulmonary Infection", Pediatr. Pulmonol., (2007) 42(S30):304.
Sagel et al., "Sputum biomarkers of inflammation in cystic fibrosis lung disease", Proc. Am. Thorac. Soc. (2007) 4:406-417.
Sato, et al., "Antimicrobial activity of DU-6859, a new potent fluoroquinolone, against clinical isolates", Antimicrob Agents Chemother. (1992) 36(7):1491-1498.
Scheinberg et al., "Nebulized Antibiotics for the Treatment of Acute Exacerbations of Chronic Rhinosinusitis", Ear, Nose & Throat J. (2002) 81:648-652.
Seemungal et al., "Long-term erythromycin therapy is associated with decreased chronic obstructive pulmonary disease exacerbations", Am J Respir Crit Care Med (2008) 178:1139-1147.
Sethi et al., "New strains of bacteria and exacerbations of chronic obstructive pulmonary disease", n. Engl J Med 347(7):465-471. (2002).
Shalit et al., "Immunomodulatory and protective effects of moxifloxacin against *Candida albicans*-induced bronchopneumonia in mice Injected with cyclophosphamide", Antimicrobial Agents and Chemotherapy (2002) 46(8):2442-2449.
Shalit et al., "Anti-inflammatory effects of moxifloxacin on IL-8, IL-1B and TNF-a secretion and NFκB and Map-kinase activation in human monocytes stimulated with *Aspergillus fumigatus*", Journal of Antimicrobial Chemotherapy (2006) 57:230-235.
Shinkai et al., "Clarithromycin has an immunomodulatory effect on ERK-mediated inflammation induced by *Pseudomonas aeruginosa* flagellin", Journal of Antimicrobial Chemotherapy (2007) 59:1096-1101.
Shinkai et al., "Macrolide antibiotics as immunomodulatory medications: Proposed mechanisms of action, Pharmacology & Therapeutics" (2008) 117:393-405.
Skauge et al., "Interaction Between Ciprofloxacin and DNA Mediated by Mg2+-ions", Inorganica Chimica Acta (2002) 339: 239-247.
Smith et al., "Chemistry and Mechanisms of Action of the Quinolone Antibacterials", The Quinolones, Academic Press Limited, Harcourt Brace Janovich, Publishers (1988) pp. 23-82.
Soler et al., "Airway inflammation and bronchial microbial patterns in patients with stable chronic obstructive pulmonary disease", Eur Respir J (1999) 14:1015-1022.
Stephenson, "Applications of x-ray powder diffraction in the pharmaceutical industry", The Rigaku Journal (2005) 22(1):2-15.
Stockley et al., "Relationship of sputum color to nature and outpatient management of acute exacerbations of COPD", Chest (2000) 117: 1638-1645.
Strieter, "Interleukin-8: a very important chemokine of the human airway epithelium", Am J Physiol Lung Cell Mol Physiol, (2002) 283:L688-689.
Suman et al., "Comparison of nasal deposition and clearance of aerosol generated by a nebulizer and an aqueous spray pump" Pharma Res. (1999) 16:1648-1652.
Suman et al., "Validity of in vitro tests on aqueous spray pumps as surrogates for nasal deposition", Pharmaceutical Research (2002) 19(1):1-6.
Suzuki et al., "Histopathological Study of the Effects of a Single Intratracheal Instillation of Surface Active Agents on Lung in Rats", The Journal of Toxicological Sciences (2000) 25(1):49-55.
Takeyama et al., "The 6-Fluoro-8-Methoxy Quinolone Gatifloxacin Down-Regulates Interleukin-8 Production in Prostate Cell Line PC-3", Antimicrobial Agents and Chemotherapy (2007) 51(1):162-168.
Takizawa et al., "Erythromycin Modulates IL-8 expression in normal and inflamed human bronchial epithelial cells", Am. J. Respir. Crit. Care Med. (1997) 156:266-271.
Traczewski et al., "In Vitro Activity of Doripenem Against *P. aeruginosa* and *Burkholderia cepacia* Isolates from Both Cystic Fibrosis and Non-cystic Fibrosis Patients," Antimicrob. Agents Chemother., (2006) 50:819-21.
Tsai et al., "Azitromycin blocks neutrophil recruitment in *Pseudomonas* endobronchial infection", Am. J. respir Crit. Care Med. (2004) 170, pp. 1331-1339.
Tsapis et al., "Direct lung delivery of para-aminosalicylic acid by aerosol particles" Tuberculosis (Edinburgh, Scotland) (England) (2003) 83(6):379-85. (Abstract Only).
Turel et al., "Biological activity of some magnesium(II) complexes of quinolones", (2000) 7(2):101-104.
Vaughan et al., "Use of nebulized antibiotics for acute infections in chronic sinusitis", Otolaryngology—Head & Neck Surgery (2002) 127:558-68.
Vaughan, "Nebulization of antibiotics in management of sinusitis", Curr. Infect. Dis. Reports. (2004) 6:187-190.
Villeneuve et al., "Nebulized Magnesium Sulfate in the Management of Acute Exacerbations of Asthma", The Annals of Pharmacotherapy (2006) 40:1118.
Wada et al., "Immunomodulatory effect of gatifloxacin on mouse peritoneal macrophages in vitro ano in models of endotoxin-induced rat conjunctivitis and rabbit bacterial keratitis", Opthalmic Res. (2008) 40:54-60.
Wahl et al. "New Medical Management Techniques for Acute Exacerbations of Chronic Rhinosinusitis", Curr Opin Otolaryngol Head Neck Surg. (2003) 11:27-32.
Wang et al. "Synthesis and crystal structure of a new copper (II) complex containing fluoroquinolone", Inter'l Symposium on Solid State Chemistry in China; Frontiers of Solid State Chemistry, World Scientific (2002) 327-332.
Weber et al., "Nebulizer Delivery of Tobramycin to the Lower Respiratory Tract", Pediatric Pulmonology, Wiley-Liss, Inc. (1994) 17: p. 331-339.
Weber et al. "Effect of nebulizer type and antibiotic concentration on device performance", Pediatric Pulmonology (1997) 23(4):249-260.
Weiss et al., "Anti-inflammatory effects of moxifloxacin on activated human monocytic cells: inhibition of NF-κB and mitogen-activated protein kinase activation and of synthesis of proinflammatory cytokines," Antimicrobial Agents and Chemotherapy, (2004) 48(6):1974-1982.
Werber et al., "Moxifloxacin inhibits cytokine-induced MAP kinase and NF-κb activation as well as nitric oxide synthesis in a human respiratory epithelial cell line", Journal of Antimicrobial Chemotherapy (2005) 55:293-300.
Wilkinson et al., "Airway bacterial load and FEV1 decline in patients with chronic obstructive pulmonary disease", Am J Respir Crit Care Med (2003) 167:1090-1095.
Wilkinson et al., "Effect of interactions between lower airway bacterial and rhinoviral infection in exacerbations of COPD", Chest (2006) 129: 317-324.
Williams, "Fluoroquinolones for respiratory infections: too valuable to overuse", Chest (2001) 120:1771-1775.

(56) References Cited

OTHER PUBLICATIONS

Yamamoto et al., "Treatment of respiratory and urinary tract infections in elderly inmates at a nursing home by selective antimicrobial agents based on the sensitivity of the isolated bacteria" Nippon Ronen Igakkai zasshi. Japanese journal of geriatrics (Japan) (2007) 44(3):359-66. (Abstract Only).

Zach, M., "Discussion", Chest (1988) 94:160S-162S.

Zhang et al., "Besifloxacin, a novel fluoroquinolone antimicrobial agent, exhibits potent inhibition of pro-inflammatory cytokines in human THP-1 monocytes", Journal of Antimicrobial Chemotherapy (2008) 61:111-116.

Zhao et al., "Description and Clinical Treatment of an Early Outbreak of Severe Acute Respiratory Syndrome (SARS) in Guangzhou, PR China" Journal of Medical Microbio. (2003) 52(8):715-720.

Zheng et al., "Pulmonary delivery of a dopamine D-1 agonist, ABT-431, in dogs and humans" Int J Pharm. (1999) 191(2):131-40. (Abstract Only).

Zimmermann et al., "Anti-inflammatory effects of antibacterials on human bronchial epithelial cells," Respiratory Research (2009) 10(89):1-8.

International Preliminary Report on Patentability dated Nov. 29, 2007 for International Patent Application No. PCT/US2006/019351, filed May 18, 2006.

International Search Report and Written Opinion dated Oct. 20, 2006 for International Patent Application No. PCT/US2006/019351, filed May 18, 2006.

International Preliminary Report on Patentability dated Aug. 28, 2008 for International Patent Application No. PCT/US2007/003649, filed Feb. 12, 2007.

International Search Report and Written Opinion dated Oct. 25, 2007 for International Patent Application No. PCT/US2007/003649, filed Feb. 12, 2007.

International Preliminary Report on Patentability dated Aug. 31, 2010, for International Patent Application No. PCT/US2009/059740, filed Oct. 6, 2009.

International Search Report and Written Opinion dated Jan. 21, 2010, for International Patent Application No. PCT/US2009/059740, filed Oct. 6, 2009.

International Search Report and Written Opinion dated Dec. 17, 2009, for International Patent Application No. PCT/US2009/059744, filed Oct. 6, 2009.

International Preliminary Report on Patentability dated Apr. 12, 2011, for International Patent Application No. PCT/US2009/059744, filed Oct. 6, 2009.

International Search Report and Written Opinion dated Jul. 30, 2010, for International Patent Application No. PCT/US2010/032128, filed Apr. 22, 2010.

International Search Report and Written Opinion dated Dec. 7, 2010, for International Patent Application No. PCT/US2010/047903, filed Sep. 3, 2010.

International Search Report and Written Opinion dated Oct. 20, 2010, for International Patent Application No. PCT/US2010/002307, filed Aug. 19, 2010.

IPOS Search Report, Written Opinion and Invitation to Response to Written Opinion, dated Aug. 12, 2010 for Singapore Patent Application No. 200717702-5.

\* cited by examiner

TOPICAL USE OF LEVOFLOXACIN FOR REDUCING LUNG INFLAMMATION

CROSS-REFERENCE TO RELATED APPLICATIONS

This application claims priority to U.S. Provisional Application No. 61/103,496, entitled "Topical Use of Levofloxacin for Reducing Lung Inflammation," filed on Oct. 7, 2008, which is hereby incorporated by reference in its entirety.

FIELD OF THE INVENTION

The present invention relates to methods and compositions for the treatment of pulmonary inflammation. In particular, methods and compositions using aerosol levofloxacin or ofloxacin to reduce pulmonary inflammation are provided.

BACKGROUND

Inflammation is a response of vascularized tissue to injury; it is perceived as redness, heat, swelling, and pain and is usually accompanied by loss of function to varying degrees. In its acute form it is of short duration, involving increased vascular transudation and interstitial edema and infiltration of inflammatory cells, predominantly of neutrophils. In moist mucosal tissues, such as that which lines the respiratory tract, there may also be loss of surface epithelial cells and secretion of mucus. This form of inflammatory response is considered protective and is, therefore, in the short term, beneficial to the host. However, if the injury is repeated or severe, the character of the inflammatory infiltrate may change to one predominantly of mononuclear cell (i.e., lymphocytes, monocytes, and macrophages) and it may become persistent.

Inflammatory diseases afflict millions of people across the world leading to suffering, economic loss and premature death. As well as inflammatory lung diseases such as asthma, chronic obstructive pulmonary disease (COPD), other inflammatory diseases include allergic rhinitis, rheumatoid arthritis, osteoarthritis, inflammatory bowel disease, and psoriasis. Inflammatory sinus diseases include sinusitis due to infections of acute, subacute and chronic duration; allergic rhinitis; and inflammation due to other underlying causes such as allergies, hay fever, allergic rhinitis, rhinitis, and asthma, affecting the nasal cavity or the four sinuses, each which have left and right halves, the frontal sinuses, the maxillary sinuses the ethmoid sinuses, and the sphenoid sinuses.

Chronic inflammation may develop from unresolved symptomatic acute inflammation or may evolve insidiously over a period of months without apparent acute onset of clinical manifestations. Histopathologic features of chronic inflammation include the predominance of macrophages and lymphocytes, proliferation of nurturing structurally heterogeneous and hyperpermeable small blood vessels, fibrosis, and necrosis. Activated macrophages and lymphocytes are interactive in releasing inflammatory mediators or cytokines that amplify immune reactivity. Cytokines include a family of biologic response modifiers including interleukins, chemokines, interferons, growth factors, and leukocyte colony-stimulating factors. The cytokines are secreted by leukocytes, connective tissue cells, and endothelial cells. Chemokines consist of 8- to 10-kd proteins that stimulate leukocyte recruitment and migration as part of the host response to antigenic insults. In chronic inflammation, the protracted inflammatory response is often accompanied simultaneously by tissue destruction and repair.

SUMMARY

The present invention relates to methods and compositions for the treatment of pulmonary inflammation. In particular, methods and compositions using aerosol levofloxacin or ofloxacin to reduce pulmonary inflammation are provided.

Some embodiments include methods for treating a pulmonary inflammation in a subject in which the methods include administering to the subject in need thereof an aerosol of a solution including levofloxacin or ofloxacin and a divalent or trivalent cation.

Figure 4A:
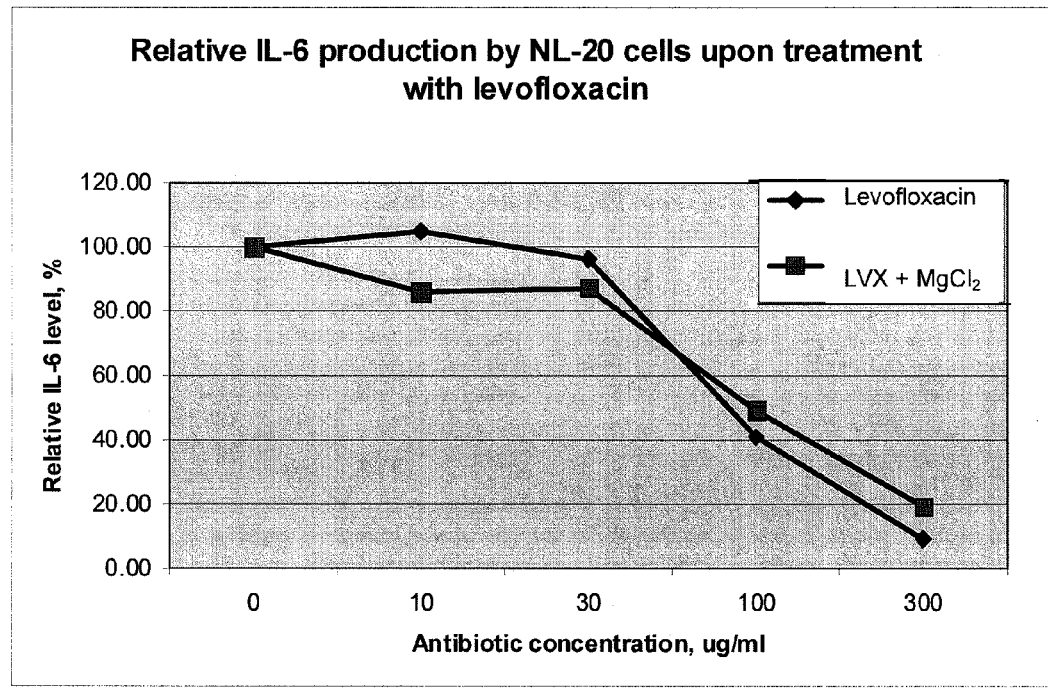
Figure 4B:
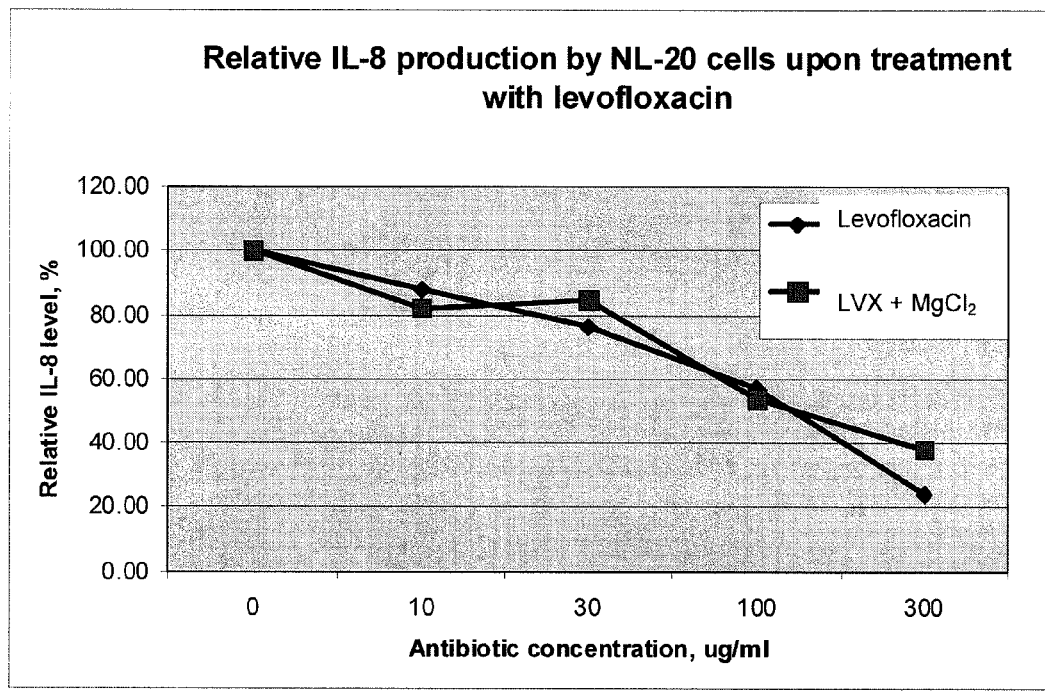
Figure 4C:
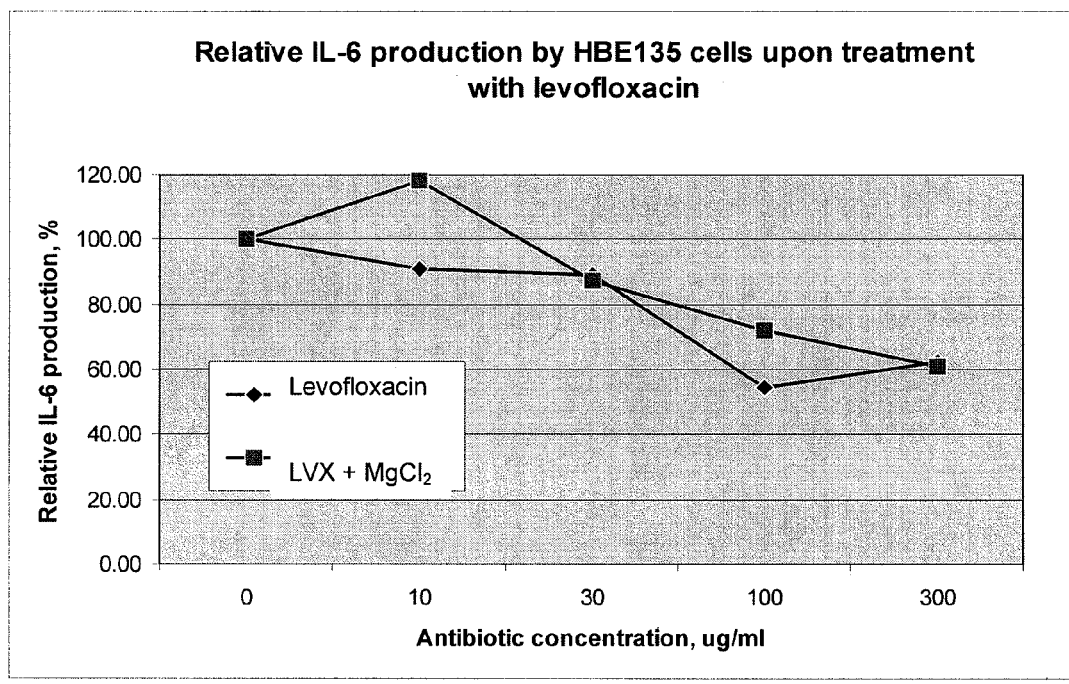
Figure 4D:
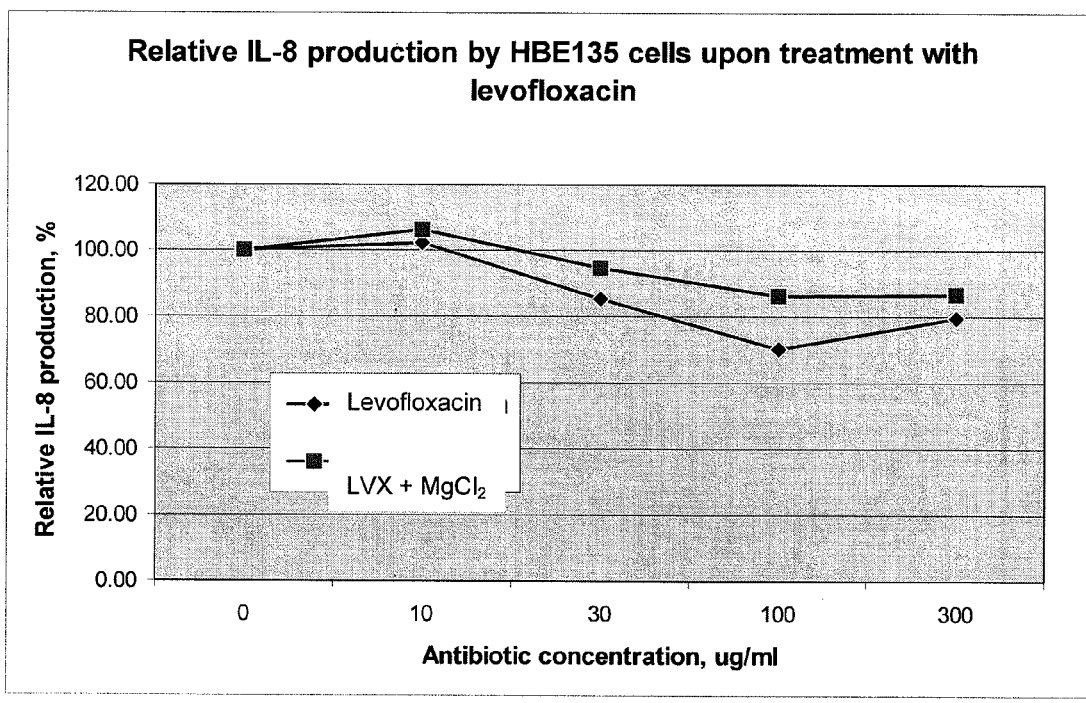

Some embodiments include methods for treating a pulmonary inflammation in a subject, wherein the pulmonary inflammation is induced by one or more pro-inflammatory cytokines, in which the methods include administering to the subject in need thereof an aerosol of a solution including levofloxacin or ofloxacin and a divalent or trivalent cation to achieve a reduction in the pulmonary concentration of said cytokine by at least 10%.

Some embodiments include methods for treating a pulmonary inflammation in a subject in which the methods include administering to the subject in need thereof an aerosol of a solution including levofloxacin or ofloxacin and a divalent or trivalent cation to achieve a reduction in the pulmonary concentration of one or more pro-inflammatory cytokines including IL-1β, IL-6 and IL-8, whereby the pulmonary inflammation is reduced or suppressed.

Some embodiments include methods for treating a pulmonary inflammation in a subject, wherein the pulmonary inflammation is induced by one or more mediators including TNFα and LPS, in which the methods include administering to the subject in need thereof an aerosol of a solution including levofloxacin or ofloxacin and a divalent or trivalent cation.

Some embodiments include methods for reducing the pulmonary concentration of a pro-inflammatory cytokine in a subject, in which the methods include administering to the subject in need thereof an aerosol of a solution including levofloxacin or ofloxacin and a divalent or trivalent cation, whereby the pulmonary concentration of the cytokine is reduced.

BRIEF DESCRIPTION OF THE DRAWINGS

FIG. 1A shows a graph of IL-6 levels produced by NL20 cells in response to treatment with control, TNFα, and TNFα with levofloxacin, moxifloxacin, or ciprofloxacin. FIG. 1B shows a graph of IL-8 produced by NL20 cells in response to treatment with control, TNFα, and TNFα with levofloxacin, moxifloxacin, or ciprofloxacin.

FIG. 2A shows a graph of IL-6 levels produced by HBE135 cells in response to treatment with control, LPS, and LPS with levofloxacin, moxifloxacin, or ciprofloxacin. FIG. 2B shows a graph of IL-8 produced by HBE135 cells in response to treatment with control, LPS, and LPS with levofloxacin, moxifloxacin, or ciprofloxacin.

FIG. 3A shows a graph of percentage cell survival for NL20 cells treated with increasing concentrations of levofloxacin, moxifloxacin, or ciprofloxacin.

FIG. 3B shows a graph of percentage cell survival for HBE135 cells treated with increasing concentrations of levofloxacin, moxifloxacin, or ciprofloxacin.

FIG. 4A shows a graph of relative IL-6 levels produced by NL20 cells treated with TNF-α in response to increasing concentrations of levofloxacin and levofloxacin formulated with MgCl$_2$. FIG. 4B shows a graph of relative IL-8 levels produced by NL20 cells treated with TNF-α in response to increasing concentrations of levofloxacin and levofloxacin formulated with MgCl$_2$. FIG. 4C shows a graph of relative IL-6 levels produced by HBE135 cells treated with LPS in response to increasing concentrations of levofloxacin and levofloxacin formulated with MgCl$_2$. FIG. 4D shows a graph of relative IL-8 levels produced by HBE cells treated with LPS in response to increasing concentrations of levofloxacin and levofloxacin formulated with MgCl$_2$.

Figure 5:
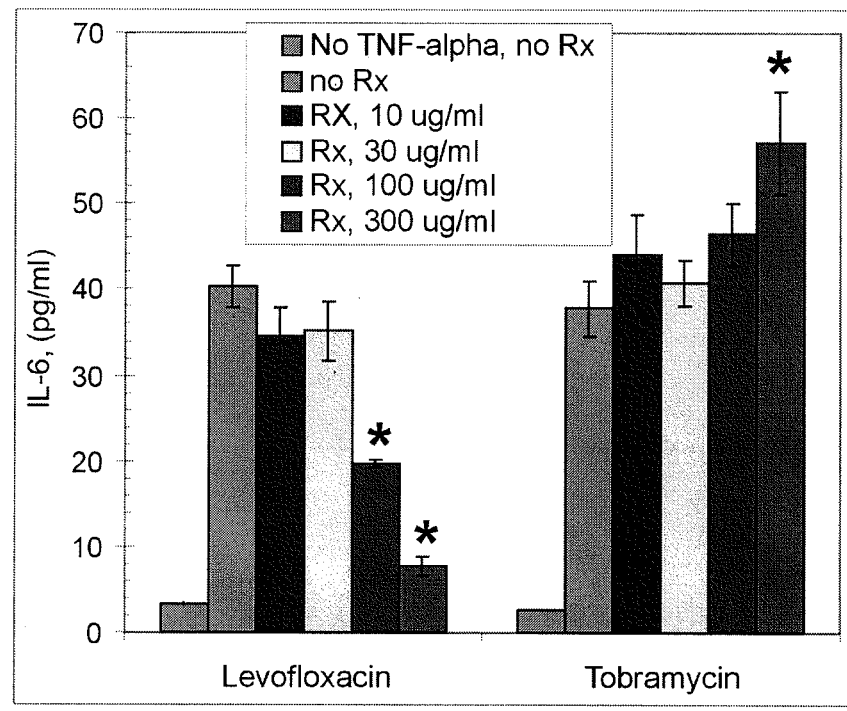
Figure 5:
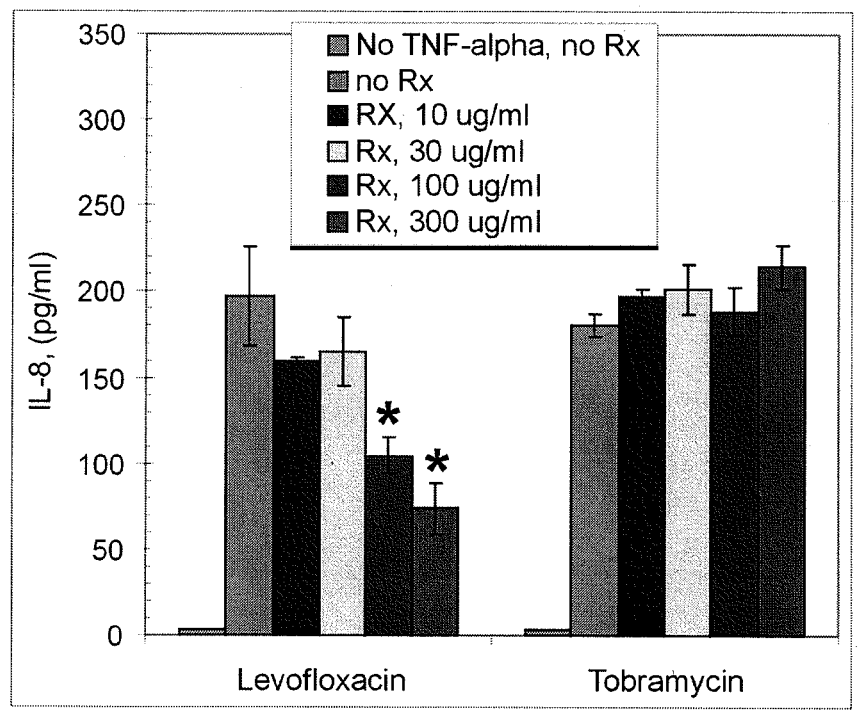

FIG. 5A shows a graph of IL-6 levels produced by NL20 cells in response to treatment with control, TNF-α, and TNF-α with 10 µg/ml, 30 µg/ml, 100 µg/ml, or 300 µg/ml levofloxacin or tobramycin. FIG. 5B shows a graph of IL-8 levels produced by NL20 cells in response to treatment with control, TNFα, and TNFα with 10 µg/ml, 30 µg/ml, 100 µg/ml, or 300 µg/ml levofloxacin or tobramycin. Results are means±SD of three replicates. *P<0.005.

Figure 6:
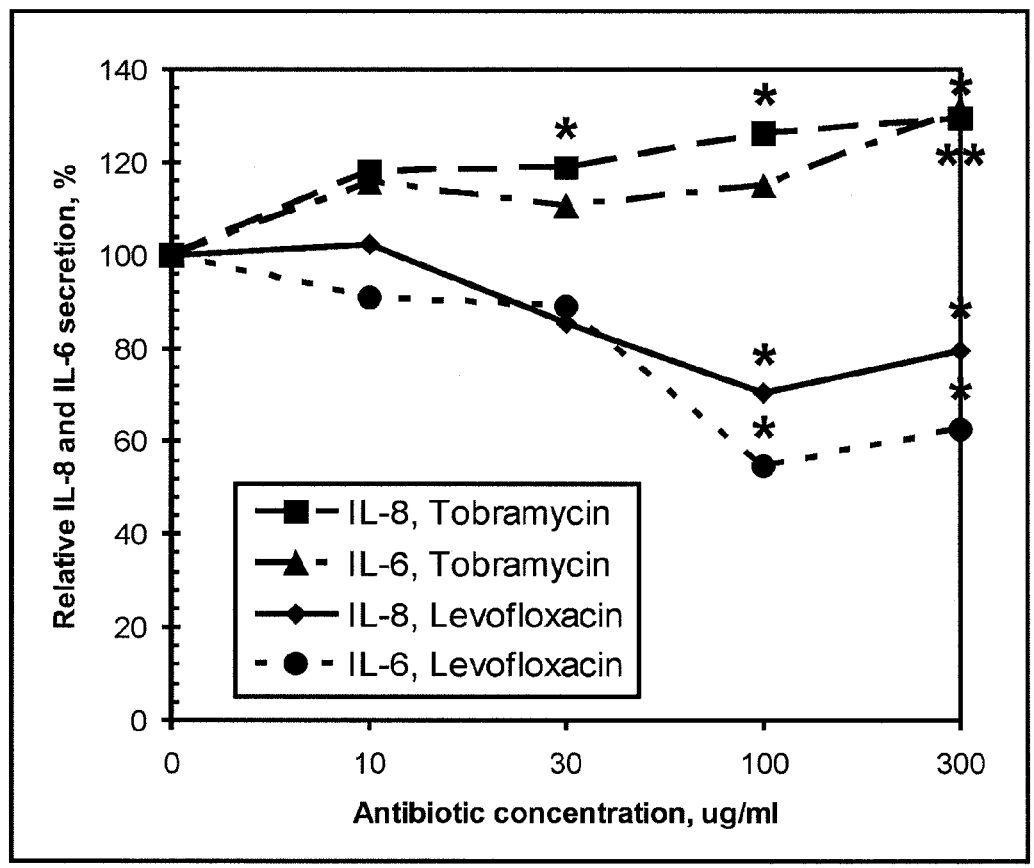

FIG. 6 shows a graph of IL-6 and IL-8 levels produced by HBE135 cells in response to treatment with LPS, and LPS with increasing concentrations of levofloxacin or tobramycin. IL-6 and IL-8 levels are shown relative to cells treated with LPS only (n=3). *P<0.05, cells treated with LPS and antibiotics compared to LPS only. **P<0.005, cells treated with LPS and antibiotics compared to LPS only.

Figure 7:
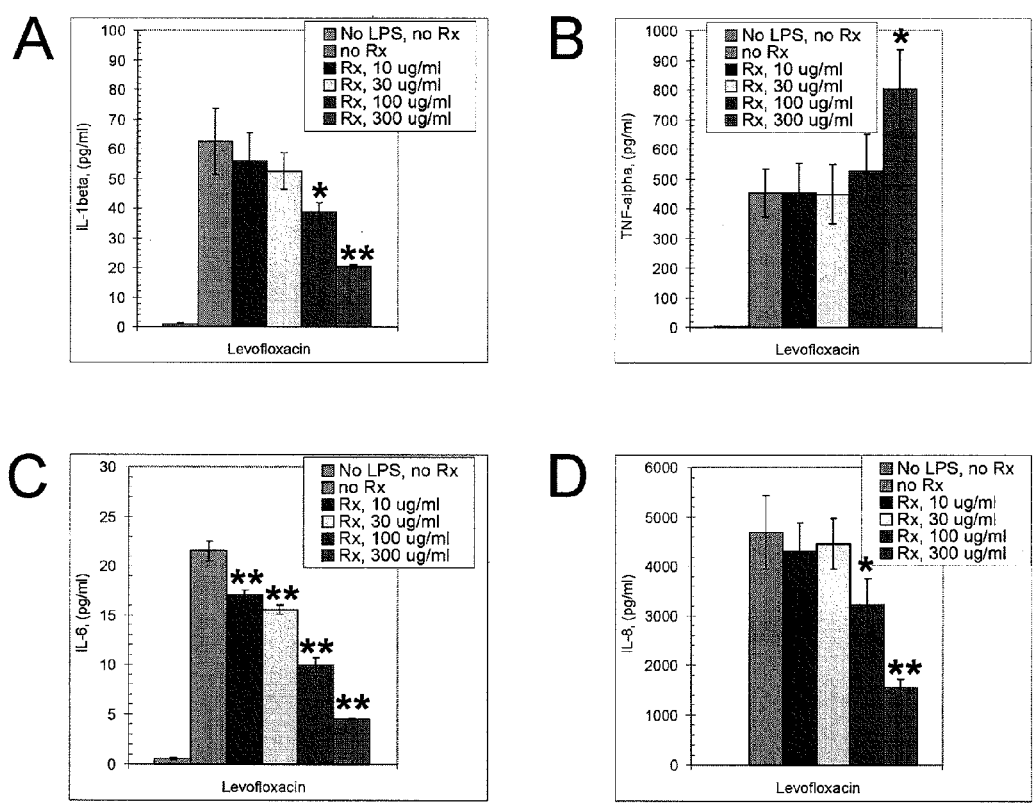

FIG. 7A shows a graph of IL-1β levels in THP-1 cells treated with control; LPS; and 10 µg/ml, 30 µg/ml, 100 µg/ml, 300 µg/ml levofloxacin and LPS. FIG. 7B shows a graph of TNFα levels in THP-1 cells treated with control; LPS; and 10 µg/ml, 30 µg/ml, 100 µg/ml, 300 µg/ml levofloxacin and LPS. FIG. 7C shows a graph of IL-6 levels in THP-1 cells treated with control; LPS; and 10 µg/ml, 30 µg/ml, 100 µg/ml, 300 µg/ml levofloxacin and LPS. FIG. 7D shows a graph of IL-8 levels in THP-1 cells treated with control; LPS; and 10 µg/ml, 30 µg/ml, 100 µg/ml, 300 µg/ml levofloxacin and LPS. Cells were incubated with LPS alone or LPS with levofloxacin for 24 h. Cytokine concentration in cell media was determined by ELISA. The results were expressed as mean±SD (n=3). *P<0.05, cells treated with LPS and antibiotics compared to LPS only. **P<0.005, for cells treated with LPS and antibiotics compared to LPS only.

Figure 8:
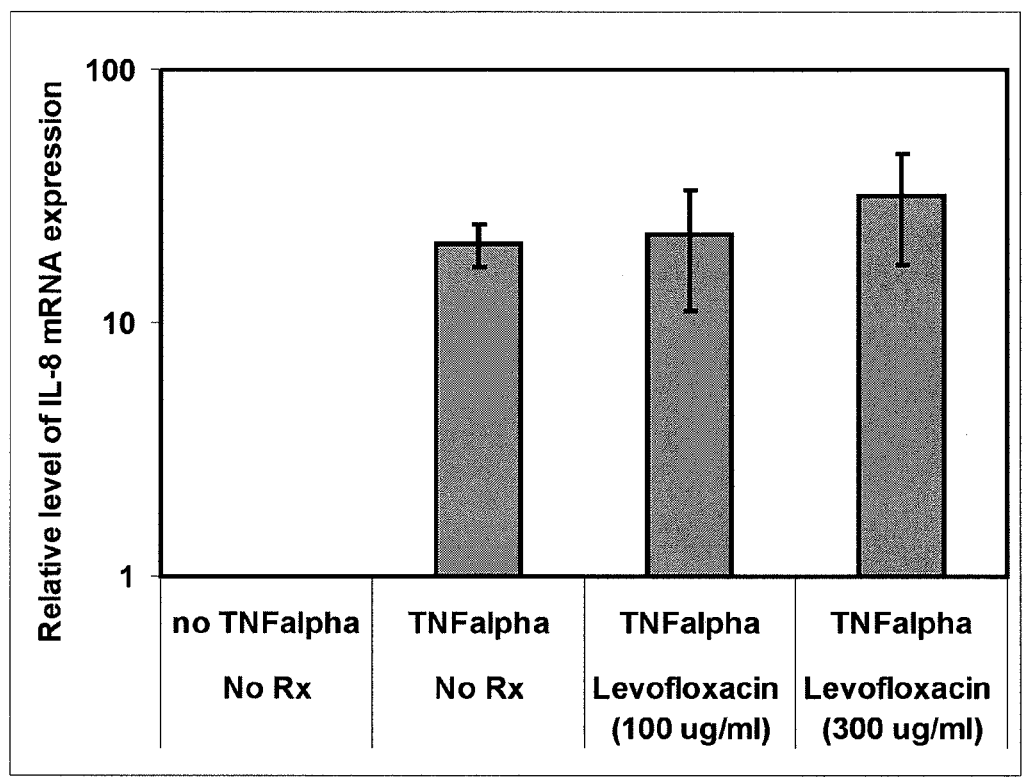

FIG. 8 shows a graph of the relative level of IL-8 mRNA in NL20 cells stimulated with control; TNFα; TNFα and 100 µg/ml levofloxacin; and TNFα and 100 µg/ml levofloxacin. Cells were seeded, serum-starved for 24 h and TNFα alone or TNFα with antibiotic were added and incubated for 24 h. Levels of mRNA were measured by real-time PCR. The results were expressed as means±SD of four replicates.

Figure 9:
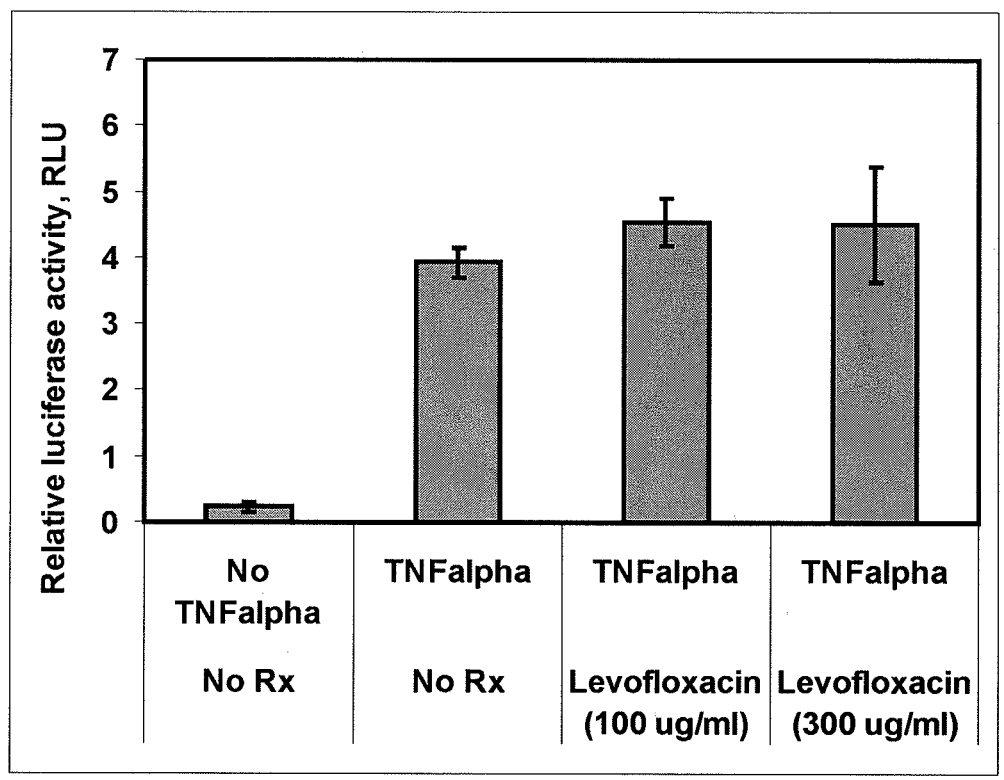

FIG. 9 shows a graph of the relative luciferase activity of a NFkB promoter construct in NL20 cells stimulated with control; TNFα; TNFα and 100 µg/ml levofloxacin; and TNFα and 100 µg/ml levofloxacin. Cells were transfected with the reporter plasmid, and after 24 h treated with TNFα alone or TNFα with antibiotics, then incubated for an additional 8 h. NFkB-dependent luciferase activity was measured using a commercial assay. The results were expressed as means±SD of six replicates.

Figure 10:
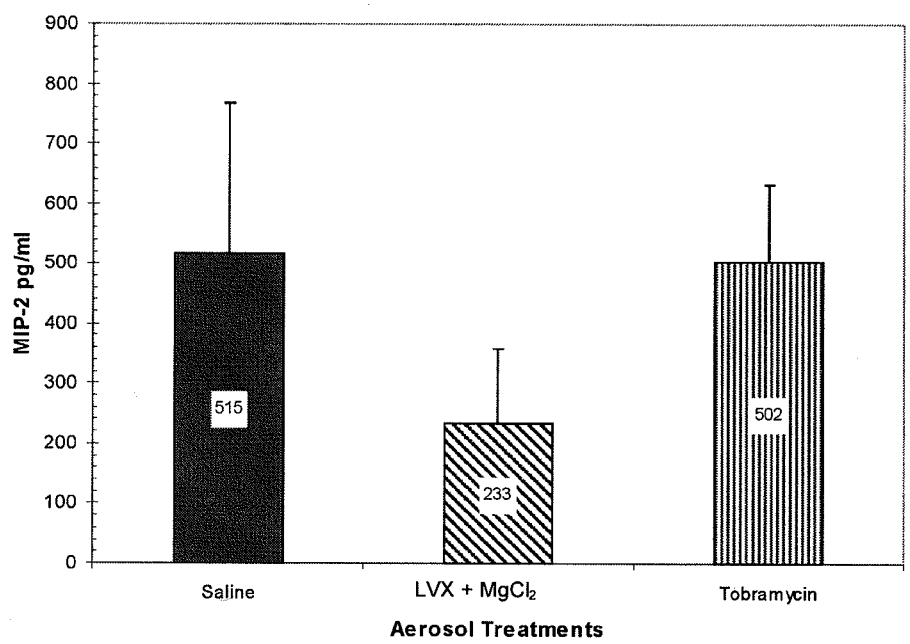
Figure 10:
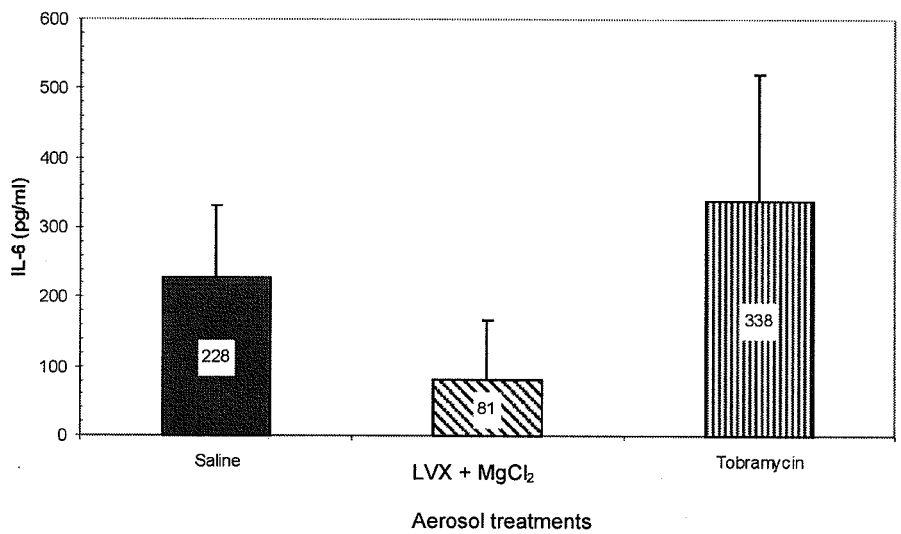

FIG. 10A shows a graph of MIP-2 levels in BAL of mice treated with 60 mg/kg saline, 60 mg/kg levofloxacin formulated with MgCl$_2$, or 60 mg/kg tobramycin. FIG. 10B shows a graph of IL-6 levels in BAL of mice treated with 60 mg/kg saline, 60 mg/kg levofloxacin formulated with MgCl$_2$, or 60 mg/kg tobramycin.

DETAILED DESCRIPTION

The present invention relates to methods and compositions for the treatment of disorders and diseases associated with pulmonary inflammation. In particular, methods and compositions to reduce inflammation using aerosol levofloxacin or ofloxacin formulated with a divalent or trivalent cation are provided. Some embodiments include treating acute or chronic inflammation of the lung or the upper airway by topically administering aerosol levofloxacin or ofloxacin formulated with a divalent or trivalent cation directly to the inflammation site.

Damage to the lungs and subsequent decline in pulmonary function that occurs in chronic inflammation is mediated primarily by neutrophil tissue infiltration that induces subsequent damage through the release of various hydrolytic and oxidative enzymes. This inflammatory cascade at the mucosal surface is mediated by bacteria producing lipopolysacchararide (LPS), and the LPS inducing TNFα release from macrophages or directly at the lung epithelial surface. Release of both TNFα, as well as inflammatory cytokines, for example IL-8 and IL-6, results in neutrophil activation and chemotaxis. While bacterial infections plays a large role in the inflammatory process, it is also believed that impaired chloride secretion in cystic fibrosis or other diseases is also partially responsible for increased cytokine levels (Perez A. et al, Am J. Physiol. Lung Cell Mol Physiol (2007) 292:383-395, incorporated by reference in its entirety).

It has been discovered that topical administration of levofloxacin formulated with divalent or trivalent cations can significantly decrease the level of cytokine and chemokine production in vitro and in vivo. Such decreases in the levels of pro-inflammatory cytokines may produce a reduction in neutrophil-mediated inflammations. Examples of pro-inflammatory cytokines include IL-1, IL-6, IL-7, and IL-8. High concentrations of levofloxacin can be administered to the lungs and upper airways by inhalation. Surprisingly, formulations of levofloxacin with divalent or trivalent cations have greater availability in the lungs compared to formulations of levofloxacin only. Accordingly, the present invention relates to methods and compositions for reducing inflammation in the lungs and upper airway by administration of aerosolized fluoroquinolones, such as levofloxacin, formulated with divalent or trivalent cations, such as $Mg^{2+}$.

Therapeutic approaches for decreasing chronic inflammation are a viable strategy to improve lung function in CF and COPD patients. Anti-inflammatory properties of non-steroidal anti-inflammatory drugs (NSAID) (e.g., ibuprofen) and azithromycin have been associated with benefits in certain CF patient subgroups (Flume P A, et al. Cystic fibrosis pulmonary guidelines: chronic medications for maintenance of lung health. Am J Respir Crit Care Med 2007; 176:957-969, incorporated by reference in its entirety). In addition, the antibiotic erythromycin reduces the incidence of pulmonary exacerbations in COPD patients (Seemungal T A, et al. Long-term erythromycin therapy is associated with decreased chronic obstructive pulmonary disease exacerbations. Am J Respir Crit Care Med 2008; 178:1139-1147, incorporated by reference in its entirety). The efficacy of azithromycin and erythromycin in these settings are likely due in large part to immunomodulatory and anti-inflammatory effects rather than antibacterial effects.

Some fluoroquinolones may have an immunomodulatory activity as well as an anti-bacterial activity. These activities may be distinct and only apparent in vivo at concentrations that are also cytotoxic. Some fluoroquinolones may affect their immunomodulatory activity through various signaling pathways that relate to the production and secretion of various cytokines and chemokines. However, not all fluoroquinolones show immunomodulatory activity. Moreover, different fluoroquinolones illicit different responses, such as the induction or inhibition of particular cytokines and chemokines. The immunomodulatory activity may also depend on cell type, immune stimulant, and concentration of the fluoroquinolone. For example, fluoroquinolones such as moxifloxacin and grepafloxacin, but not ciprofloxacin, can inhibit secretion of pro-inflammatory factor such as IL-8, IL-6, ERK1/2, JNK, and NFκB in human lung epithelia cells (Blau, H., K. et al. 2007. Moxifloxacin but not ciprofloxacin or azithromycin selectively inhibits IL-8, IL-6, ERK1/2, JNK, and NF-kappaB activation in a cystic fibrosis epithelial cell line. Am J Physiol Lung Cell Mol Physiol 292:L343-52; Donnarumma, G., I. et al. 2007. Anti-inflammatory effects of moxifloxacin and human beta-defensin 2 association in human lung epithelial cell line (A549) stimulated with lipopolysaccharide. Peptides 28:2286-92; Hashimoto, S., K. et al. 2000. Grepafloxacin inhibits tumor necrosis factor-alpha-induced interleukin-8 expression in human airway epithelial cells. Life Sci 66:PL 77-82, incorporated by reference in their entireties). However, in all studies cells were treated with antibiotic concentrations less than 50 mg/ml, which corresponds to serum drug concentrations that may be attained after systemic dosing.

Levofloxacin inhibits TNF-α and IFNγ production in tonsillar lymphocytes at 50 mg/L, and IL-8 production at 5 mg/L. In addition, levofloxacin inhibits RANTES-release in nasal epithelial cells from patients of nasal polyposis. However, the inhibitory activity of levofloxacin on the production of pro-inflammatory factors is much lower than that for other fluoroquinolones such as ciprofloxacin and moxifloxacin. For example, the inhibitory activity of levofloxacin on the production of pro-inflammatory factors such as TNF-α, IL-1 and IL-8 requires 100 mg/L levofloxacin.

As described herein, immortalized human airway epithelia cells retain certain features of airway epithelium and have been extensively used to characterize immunomodulatory effects of other antibiotics (Blau H, et al. Moxifloxacin but not ciprofloxacin or azithromycin selectively inhibits IL-8, IL-6, ERK1/2, JNK, and NF-kappaB activation in a cystic fibrosis epithelial cell line. Am J Physiol Lung Cell Mol Physiol 2007; 292:L343-352; and Donnarumma G, et al. Anti-inflammatory effects of moxifloxacin and human beta-defensin 2 association in human lung epithelial cell line (A549) stimulated with lipopolysaccharide. Peptides 2007; 28:2286-2292, incorporated by reference in their entireties). IL-6 and IL-8 production in those cells can be strongly induced by TNFα or by bacterial LPS that is present in high concentrations in lung fluids of CF and COPD patients (Sagel S D, et al. Sputum biomarkers of inflammation in cystic fibrosis lung disease. Proc Am Thorac Soc 2007; 4:406-417, incorporated by reference in its entirety). Both IL-6 and IL-8 are of high importance in regulating inflammatory response in CF lungs, with latter having the strongest potential to induce neutrophil chemotaxis (Strieter R M. Interleukin-8: a very important chemokine of the human airway epithelium. Am J Physiol Lung Cell Mol Physiol 2002; 283:L688-689, incorporated by reference in its entirety). It has been discovered that levofloxacin produces a dose-dependent reduction of TNFα- and LPS-induced IL-6 and IL-8 levels in cultured human airway epithelia cells. Levofloxacin also decreases LPS-induced IL-1 IL-6 and IL-8 production in human monocytic cells. In addition, levofloxacin reduces IL-6 and IL-8 production in vivo.

DEFINITIONS

The term "administration" or "administering" refers to a method of giving a dosage of an anti-inflammatory pharmaceutical composition to a vertebrate. The preferred method of administration can vary depending on various factors, e.g., the components of the pharmaceutical composition, the site of the inflammation, and the severity of an actual inflammation.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, incorporated by reference herein in its entirety.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, naphtoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsufuric acid, naphthalene-1,5-disulfonic acid, naphthalene-2-sulfonic acid, and saccharin.

"Solvate" refers to the compound formed by the interaction of a solvent and fluoroquinolone antimicrobial, a metabolite, or salt thereof. Suitable solvates are pharmaceutically acceptable solvates including hydrates.

By "therapeutically effective amount" or "pharmaceutically effective amount" is meant a fluoroquinolone anti-inflammatory agent, as disclosed for this invention, which has a therapeutic effect. The doses of fluoroquinolone anti-inflammatory agent which are useful in treatment are therapeutically effective amounts. Thus, as used herein, a therapeutically effective amount means those amounts of fluoroquinolone anti-inflammatory agent which produce the desired therapeutic effect as judged by clinical trial results and/or model animal anti-inflammatory studies. In particular embodiments, the fluoroquinolone anti-inflammatory agent are administered in a pre-determined dose, and thus a therapeutically effective amount would be an amount of the dose administered. This amount and the amount of the fluoroquinolone anti-inflammatory agent can be routinely determined by one of skill in the art, and will vary, depending on several factors, such as the particular inflammation involved, for example, the site of inflammation, the severity of inflammation. This amount can further depend upon the patient's height, weight, sex, age and medical history. For prophylactic treatments, a therapeutically effective amount is that amount which would be effective to prevent a particular inflammation.

A "therapeutic effect" relieves, to some extent, one or more of the symptoms of the inflammation, and includes curing an inflammation. "Curing" means that the symptoms of inflammation are eliminated. However, certain long-term or permanent effects of the inflammation may exist even after a cure is obtained (such as extensive tissue damage). As used herein, a "therapeutic effect" is defined as a statistically significant reduction in an inflammation, emergence of inflammation, or improvement in inflammation symptoms as measured by human clinical results or animal studies.

"Treat," "treatment," or "treating," as used herein refers to administering a pharmaceutical composition for prophylactic and/or therapeutic purposes. The term "prophylactic treatment" refers to treating a patient who is not yet having an inflammation, but who is susceptible to, or otherwise at risk of, a particular inflammation such that there is a reduced onset of an inflammation. The term "therapeutic treatment" refers to administering treatment to a patient already suffering from an inflammation. Thus, in preferred embodiments, treating is the administration to a mammal (either for therapeutic or prophylactic purposes) of therapeutically effective amounts of a fluoroquinolone anti-inflammatory agent.

The term "dosing interval" refers to the time between administrations of the two sequential doses of a pharmaceutical's during multiple dosing regimens. For example, in the case of orally administered ciprofloxacin, which is administered twice daily (traditional regimen of 400 mg b.i.d) and orally administered levofloxacin, which is administered once a day (500 mg or 750 mg q.d.), the dosing intervals are 12 hours and 24 hours, respectively.

As used herein, the "peak period" of a pharmaceutical's in vivo concentration is defined as that time of the pharmaceutical dosing interval when the pharmaceutical concentration is not less than 50% of its maximum plasma or site-of-inflammation concentration. In some embodiments, "peak period" is used to describe an interval of anti-inflammatory dosing.

The "respirable delivered dose" is the amount of drug inhaled during the inspiratory phase of the breath simulator that is equal to or less than 5 microns using a simulator programmed to the European Standard pattern of 15 breaths per minute, with an inspiration to expiration ratio of 1:1.

As used herein "pulmonary concentration" can include the concentration of a substance in the lung of a subject, the concentration of a substance in the sputum of a subject, and/or the concentration of a substance in the bronchial alveoial lavage of a subject. As will be understood, "pulmonary concentration" can be measured by various methods.

Methods of Treatment or Prophylaxis

In some embodiments, a method is provided for treating an inflammation in an animal, specifically including in a mammal, by treating an animal suffering from such an inflammation with a fluoroquinolone anti-inflammatory agent formulated with a divalent or trivalent cation and having improved pulmonary availability. In some embodiments, fluoroquinolone anti-inflammatory agents may be administered following aerosol formation and inhalation. Thus, this method of treatment is especially appropriate for the treatment of pulmonary inflammations that are difficult to treat using an anti-inflammatory agent delivered parenterally due to the need for high parenteral dose levels (which can cause undesirable side effects), or due to lack of any clinically effective anti-inflammatory agents. In one such embodiment, this method may be used to administer a fluoroquinolone anti-inflammatory agent directly to the site of inflammation. Such a method may reduce systemic exposure and maximizes the amount of anti-inflammatory agent to the site of inflammation.

In some embodiments, the aerosol fluoroquinolone therapy may be administered as a treatment or prophylaxis in combination or alternating therapeutic sequence with other aerosol, oral or parenteral antibiotics. By non-limiting example this may include aerosol tobramycin and/or other aminoglycoside, aerosol aztreonam and/or other beta- or mono-bactam, carbapenems, aerosol ciprofloxacin and/or other fluoroquinolones, aerosol azithromycin and/or other macrolides or ketolides, tetracycline and/or other tetracyclines, quinupristin and/or other streptogramins, linezolid and/or other oxazolidinones, vancomycin and/or other glycopeptides, erythromycin, and chloramphenicol and/or other phenicols, and colisitin and/or other polymyxins.

In addition, compositions and methods provided herein can include the aerosol fluoroquinolone therapy administered as a treatment or prophylaxis in combination or alternating therapeutic sequence with an additional active agent. As discussed above, some such additional agents can include antibiotics. More additional agents can include bronchodilators, anticholinergics, glucocorticoids, eicosanoid inhibitors, and combinations thereof. Examples of bronchodilators include salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast. Examples of anticholinergics include ipratropium, and tiotropium. Examples of glucocorticoids include prednisone, fluticasone, budesonide, mometasone, ciclesonide, and beclomethasone. Examples of eicosanoids include montelukast, pranlukast, zafirlukast, zileuton, ramatroban, and seratrodast. More additional agents can include pulmozyme, hypertonic saline, agents that restore chloride channel function in CF, inhaled beta-agonists, inhaled antimuscarinic agents, inhaled corticosteroids, and inhaled or oral phosphodiesterase inhibitors. More additional agents can include CFTR modulators, for example, VX-770, atluren, VX-809. More additional agents can include agents to restore airway surface liquid, for example, denufosol, mannitol, GS-9411, and SPI-8811 More additional agents can include anti-inflammatory agents, for example, ibuprofen, sildenafil, and simavastatin. More additional agent include anti-inflammatory agents. Examples of anti-inflammatory agents include steroidal and non-steriodal anti-inflammatory agent. Examples of steroidal anti-inflammatory agents include 21-acetoxypregnenolone, alclometasone, algestone, amcinonide, beclomethasone, betamethasone, chloroprednisone, ciclesonide, clobetasol, clobetasone, clocortolone, cloprednol, corticosterone, cortisone, cortivazol, deflazacort, desciclesonide, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, analogues, and combinations thereof. Examples of nonsteriodal anti-inflammatory agents include COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide).

Pharmaceutical Compositions

For purposes of the method described herein, a fluoroquinolone anti-inflammatory agent formulated with a divalent or trivalent cation having improved pulmonary availability may be administered using an inhaler. In some embodiments, a fluoroquinolone anti-inflammatory agent disclosed herein is produced as a pharmaceutical composition suitable for aerosol formation, good taste, storage stability, and patient safety and tolerability. In some embodiments, the isoform content of the manufactured fluoroquinolone may be optimized for tolerability, anti-inflammatory activity and stability.

Formulations can include a divalent or trivalent cation. The divalent or trivalent cation can include, for example, magnesium, calcium, zinc, copper, aluminum, and iron. In some embodiments, the solution comprises magnesium chloride, magnesium sulfate, zinc chloride, or copper chloride. In some embodiments, the divalent or trivalent cation concentration can be from about 25 mM to about 400 mM, from about 50 mM to about 400 mM, from about 100 mM to about 300 mM, from about 100 mM to about 250 mM, from about 125 mM to about 250 mM, from about 150 mM to about 250 mM, from about 175 mM to about 225 mM, from about 180 mM to about 220 mM, and from about 190 mM to about 210 mM. In some embodiments, the chloride concentration can be from about 25 mM to about 800 mM, from about 50 mM to about 400 mM, from about 100 mM to about 300 mM, from about 100 mM to about 250 mM, from about 125 mM to about 250 mM, from about 150 mM to about 250 mM, from about 175 mM to about 225 mM, from about 180 mM to about 220 mM, and from about 190 mM to about 210 mM. In some embodiments, the magnesium chloride, magnesium sulfate, zinc chloride, or copper chloride can have a concentration from about 5% to about 25%, from about 10% to about 20%, and from about 15% to about 20%. In some embodiments, the ratio of fluoroquinolone to divalent or trivalent cation can be 1:1 to 2:1 or 1:1 to 1:2.

Non-limiting fluoroquinolones for use as described herein include levofloxacin, ofloxacin, ciprofloxacin, enoxacin, gatifloxacin, gemifloxacin, lomefloxacin, moxifloxacin, norfloxacin, pefloxacin, sparfloxacin, garenoxacin, sitafloxacin, and DX-619.

The formulation can have a fluoroquinolone concentration, for example, levofloxacin or ofloxacin, greater than about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, and about 200 mg/ml. In some embodiments, the formulation can have a fluoroquinolone concentration, for example, levofloxacin or ofloxacin, from about 50 mg/ml to about 200 mg/ml, from about 75 mg/ml to about 150 mg/ml, from about 80 mg/ml to about 125 mg/ml, from about 80 mg/ml to about 120 mg/ml, from about 90 mg/ml to about 125 mg/ml, from about 90 mg/ml to about 120 mg/ml, and from about 90 mg/ml to about 110 mg/ml.

The formulation can have an osmolality from about 300 mOsmol/kg to about 500 mOsmol/kg, from about 325 mOsmol/kg to about 450 mOsmol/kg, from about 350 mOsmol/kg to about 425 mOsmol/kg, and from about 350 mOsmol/kg to about 400 mOsmol/kg. In some embodiments, the osmolality of the formulation is greater than about 300 mOsmol/kg, about 325 mOsmol/kg, about 350 mOsmol/kg, about 375 mOsmol/kg, about 400 mOsmol/kg, about 425 mOsmol/kg, about 450 mOsmol/kg, about 475 mOsmol/kg, and about 500 mOsmol/kg.

The formulation can have a pH from about 4.5 to about 8.5, from about 5.0 to about 8.0, from about 5.0 to about 7.0, from about 5.0 to about 6.5, from about 5.5 to about 6.5, and from about 6.0 to about 6.5.

The formulation can comprise a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like), or auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). In some embodiments, the formulation can lack a conventional pharmaceutical carrier, excipient or the like. Some embodiments include a formulation lacking lactose. Some embodiments comprise lactose at a concentration less than about 10%, 5%, 1%, or 0.1%. In some embodiments, the formulation can consist essentially of levofloxacin or ofloxacin and a divalent or trivalent cation.

In some embodiments, a formulation can comprise a levofloxacin concentration between about 75 mg/ml to about 150 mg/ml, a magnesium chloride concentration between about 150 mM to about 250 mM, a pH between about 5 to about 7; an osmolality of between about 300 mOsmol/kg to about 500 mOsmol/kg, and lacks lactose.

In some embodiments, a formulation comprises a levofloxacin concentration about 100 mg/ml, a magnesium chloride concentration about 200 mM, a pH about 6.2 an osmolality about 383 mOsmol/kg, and lacks lactose. In some embodiments, a formulation consists essentially of a levofloxacin concentration about 100 mg/ml, a magnesium chloride concentration about 200 mM, a pH about 6.2 an osmolality about 383 mOsmol/kg, and lacks lactose. In some embodiments, a formulation consists of a levofloxacin concentration about 100 mg/ml, a magnesium chloride concentration about 200 mM, a pH about 6.2 an osmolality about 383 mOsmol/kg, and lacks lactose.

Administration

The fluoroquinolone anti-inflammatory agents formulated with divalent or trivalent cations and having improved pulmonary availability may be administered at a therapeutically effective dosage, e.g., a dosage sufficient to provide treatment for the disease states previously described. The amount of active compound administered will, of course, be dependent on the subject and disease state being treated, the severity of the inflammation, the manner and schedule of administration and the judgment of the prescribing physician; for example, a likely dose range for aerosol administration of levofloxacin would be about 20 to 300 mg per day, the active agents being selected for longer or shorter pulmonary half-lives, respectively. In some embodiments, a likely dose range for aerosol administration of levofloxacin would be about 20 to 300 mg BID (twice daily).

Administration of the fluoroquinolone antimicrobial agents disclosed herein or the pharmaceutically acceptable salts thereof can be via any of the accepted modes of administration for agents that serve similar utilities including, but not limited to, aerosol inhalation. Methods, devices and compositions for delivery are described in U.S. Patent Application Publication No. 2006/0276,483, incorporated by reference in its entirety.

Pharmaceutically acceptable compositions include solid, semi-solid, liquid and aerosol dosage forms, such as, for example, powders, liquids, suspensions, complexations, liposomes, particulates, or the like. Preferably, the compositions are provided in unit dosage forms suitable for single administration of a precise dose.

The fluoroquinolone anti-inflammatory agent can be administered either alone or in some alternatives, in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrin derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In one preferred embodiment, the compositions will take the form of a unit dosage form such as vial containing a liquid, solid to be suspended, dry powder, lyophilate, or other composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. However, percentages of active ingredient of 0.01% to 90% in solution are employable, and will be higher if the composition is a solid, which will be subsequently diluted to the above percentages. In some embodiments, the composition will comprise 1.0%-50.0% of the active agent in solution.

Compositions described herein can be administered with a frequency of about 1, 2, 3, 4, or more times daily, 1, 2, 3, 4, 5, 6, 7 or more times weekly, 1, 2, 3, 4, 5, 6, 7, 8, 9, 10 or more times monthly. In particular embodiments, the compositions are administered twice daily.

Aerosol Delivery

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

In one embodiment, a nebulizer is selected on the basis of allowing the formation of an aerosol of a fluoroquinolone anti-inflammatory agent disclosed herein having an MMAD predominantly between about 2 to about 5 microns. In one embodiment, the delivered amount of fluoroquinolone anti-inflammatory agent provides a therapeutic effect for respiratory infections. The nebulizer can deliver an aerosol comprising a mass median aerodynamic diameter from about 2 microns to about 5 microns with a geometric standard deviation less than or equal to about 2.5 microns, a mass median aerodynamic diameter from about 2.5 microns to about 4.5 microns with a geometric standard deviation less than or equal to about 1.8 microns, and a mass median aerodynamic diameter from about 2.8 microns to about 4.3 microns with a geometric standard deviation less than or equal to about 2 microns. In some embodiments, the aerosol can be produced a jet nebulizer. In some embodiments, the aerosol can be produced using a vibrating mesh nebulizer. An example of a vibrating mesh nebulizer includes the PARI E-FLOW® nebulizer. More examples of nebulizers are provided in U.S. Pat. Nos. 4,268,460; 4,253,468; 4,046,146; 3,826,255; 4,649,911; 4,510,929; 4,624,251; 5,164,740; 5,586,550; 5,758,637; 6,644,304; 6,338,443; 5,906,202; 5,934,272; 5,960,792;

5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303 all of which are hereby incorporated by reference in their entireties. More commercial examples of nebulizers that can be used with the formulations described herein include Respirgard II®, Aeroneb®, Aeroneb® Pro, and Aeroneb® Go produced by Aerogen; AERx® and AERx Essence™ produced by Aradigm; Porta-Neb®, Freeway Freedom™, Sidestream, Ventstream and I-neb produced by Respironics, Inc.; and PARI LC-Plus®, PARI LC-Star®, produced by PARI, GmbH. By further non-limiting example, U.S. Pat. No. 6,196,219, is hereby incorporated by reference in its entirety.

The amount of levofloxacin or ofloxacin that can be administered to the lungs can include at least about 20 mg, about 30 mg, about 40 mg, about 50 mg, about 60 mg, about 70 mg, about 80 mg, about 90 mg, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, and about 800 mg.

The aerosol can be administered to the lungs in less than about 120 minutes, about 100 minutes, about 90 minutes, about 80 minutes, about 70 minutes, about 60 minutes, about 20 minutes, about 10 minutes, about 5 minutes, about 4 minutes, about 3 minutes, about 2 minutes, and about 1 minute.

Indications

Some embodiments of the methods and compositions described herein relate to treating particular disorders and diseases associated inflammation. In particular embodiments, the inflammation can be acute or chronic inflammation of the lung or the upper airway. As used herein "pulmonary inflammation" can refer to acute or chronic inflammation of at least a portion of the respiratory tract, such as the lungs and upper airway. Examples of such disorders and diseases associated with pulmonary inflammation can include asthma, cystic fibrosis, pulmonary fibrosis, chronic bronchitis, bronchiectasis, chronic granulomatous disease, sinusitis, chronic obstructive pulmonary disease, and pneumonia.

Some embodiments include methods to achieve a reduction in pulmonary inflammation. A reduction can include reducing the signs and symptoms of a pulmonary inflammation. In some embodiments, methods include achieving a reduction in the levels of pro-inflammatory cytokines in the lungs. A reduction in the levels of pro-inflammatory cytokines in the lungs can be measured by various methods, such as a reduction in the levels of pro-inflammatory cytokines in sputum and/or BAL. In some embodiments, methods include achieving a reduction in the levels of IL-10, IL-6, and IL-8 in the lungs.

EXAMPLES

Example 1

In Vitro Activity of Levofloxacin, Ciprofloxacin and Moxifloxacin at Low Concentrations on IL-6 and IL-8 Production NL20 cells and HBE135 cells are immortalized human airway epithelial cells that retain certain features of airway epithelium and have been extensively used to characterize immunomodulatory effects of other antibiotics (Blau H, et al. Moxifloxacin but not ciprofloxacin or azithromycin selectively inhibits IL-8, IL-6, ERK1/2, JNK, and NF-kappaB activation in a cystic fibrosis epithelial cell line. Am J Physiol Lung Cell Mol Physiol 2007; 292:L343-352; and Donnarumma G, et al. Anti-inflammatory effects of moxifloxacin and human beta-defensin 2 association in human lung epithelial cell line (A549) stimulated with lipopolysaccharide. Peptides 2007; 28:2286-2292, incorporated by reference in their entireties). IL-6 and IL-8 production in the NL20 and HBE135 cells was induced by adding TNFα or Lipopolysaccharide (LPS) from Pseudomonas aeruginosa, respectively. The effect of antibiotics on cytokine levels was assessed by ELISA assay.

NL20 cells were maintained in Ham's F12 medium with 2 mM L-glutamine, 0.1 mM nonessential amino acids, 5 μg/ml insulin, 10 ng/ml epidermal growth factor, 1 μg/ml transferrin, 500 ng/ml hydrocortisone and 4% FBS. HBE135 cells were routinely grown in keratinocyte-serum free medium with 5 ng/ml of human recombinant EGF and 0.05 mg/ml of bovine pituitary extract (Invitrogen, San Diego, Calif.) supplemented with 5 μg/ml insulin and 500 ng/ml hydrocortisone.

NL20 cells were seeded on 24-well tissue culture plates at $2 \times 10^4$ cell/ml. The day after seeding, cells received normal growth medium without serum for an additional 24 h. The same serum-free media was used for all subsequent treatments of NL20 cells. IL-6 and IL-8 production in NL20 monolayers was induced by treatment with 10 ng/ml of TNFα. HBE135 Cells were aliquoted into 24-well tissue culture plates at $1 \times 10^5$ cells/ml and were used for cytokine production experiments approximately 24 hours after plating without additional media changes. IL-6 and IL-8 production in HBE135 cells was induced by treatment with 5 μg/ml of LPS from P. aeruginosa. After 48 h, cell medium was collected, clarified and the amount of IL-6 and IL-8 released into the medium was quantified using QuantiGlo chemiluminescent ELISA kits (R&D Systems, Minneapolis, Minn.). To test the effect of antibiotics on IL-6 and IL-8 secretion, antibiotics were added to culture media along with LPS or TNF-α and processed as described above.

Figure 1B:
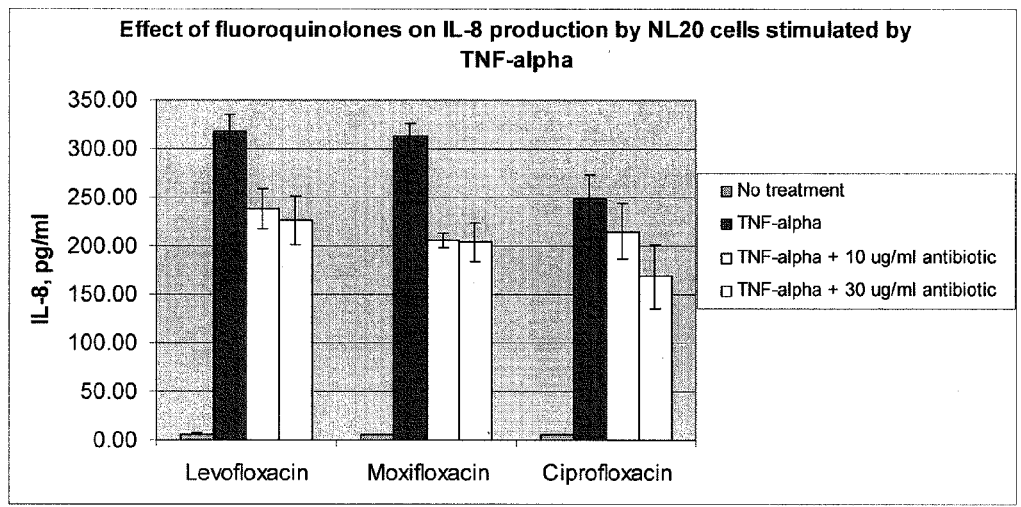
Figure 2A:
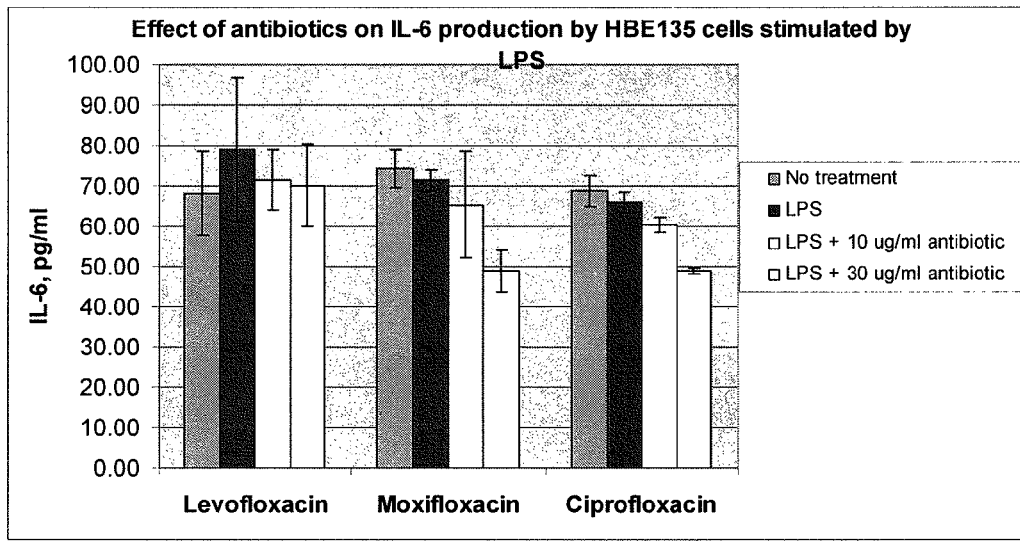
Figure 2B:
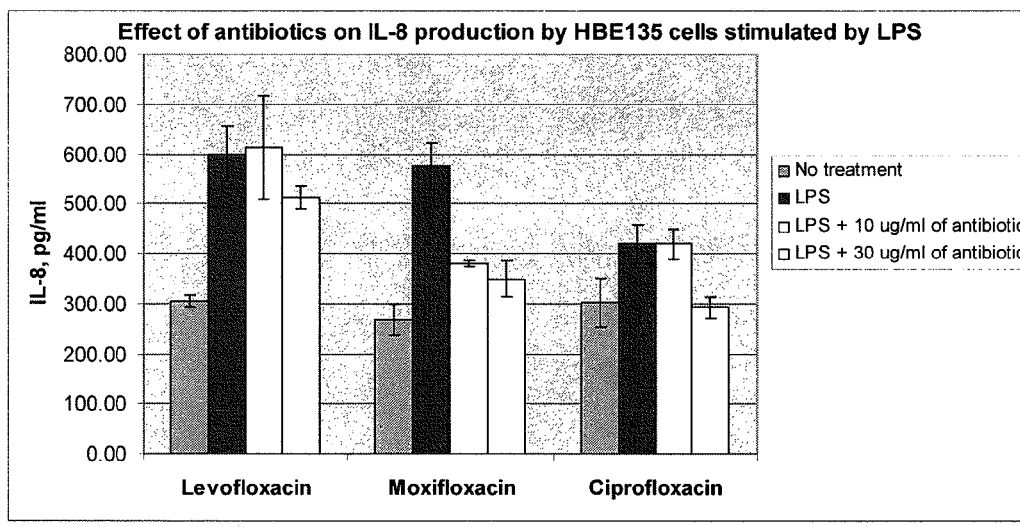

TNF-α induced a several-fold increase in IL-6 and IL-8 production in NL20 cells (FIGS. 1A and 1B). LPS induced an increase in the level of IL-8 in HBE135 cells (FIG. 2B). In NL20 cells treated with 10 μg/ml and 30 μg/ml levofloxacin, moxifloxacin or ciprofloxacin, IL-8 levels were reduced by approximately 20-30% (FIGS. 1A and 1B). No significant change in IL-6 levels was observed in cells treated with levofloxacin or ciprofloxacin. However, in NL20 cells treated with 30 μg/ml ciprofloxacin, an increase in IL-6 levels was observed. FIGS. 2A and 2B show the levels of IL-6 and IL-8 in cells. In HBE135 cells treated with 10 μg/ml and 30 μg/ml levofloxacin, moxifloxacin or ciprofloxacin. This experiment shows that low concentrations of levofloxacin can reduce the levels of IL-8 in HBE135 cells stimulated with LPS.

Example 2

In Vitro Cytotoxicity of Levofloxacin, Ciprofloxacin and Moxifloxacin

Figure 3A:
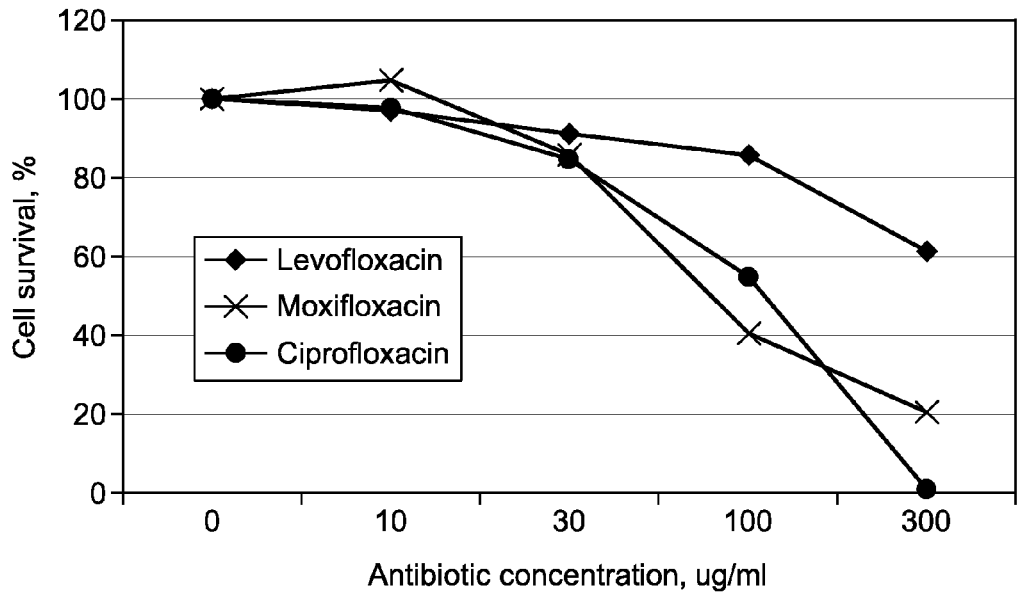
Figure 3B:
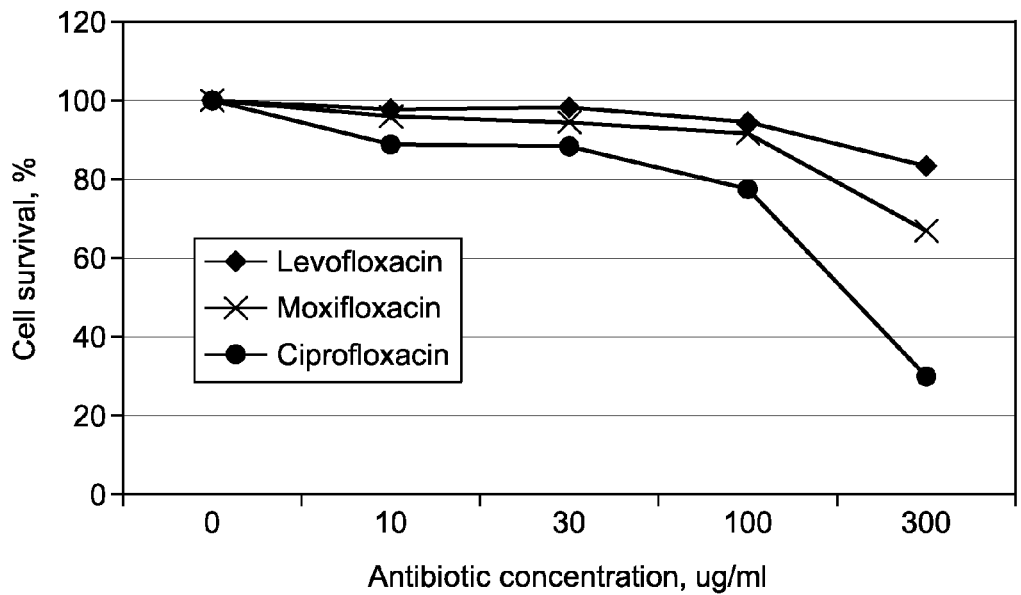

The cytotoxicity of levofloxacin, moxifloxacin and ciprofloxacin on NL20 and HBE135 cell lines were measured using an Alamar Blue assay. After 48 hour incubation with the antibiotic, cells were incubated in fresh growth media containing 5% Alamar Blue dye and fluorescence was recorded at 0 h and 4 h to assess antibiotic cytotoxicity. Higher levofloxacin concentrations were less cytotoxic to either NL20 or HBE135 cells compared to moxifloxacin and ciprofloxacin (FIGS. 3A and 3B). Moxifloxacin and ciprofloxacin were significantly cytotoxic to NL20 cells at 300 mg/ml.

Example 3

In Vitro Activity of Levofloxacin on IL-6 and IL-8 Production

NL20 cells induced with TNFα and HBE135 cells induced with LPS were treated with 300 μg/ml levofloxacin or 300 μg/ml levofloxacin formulated with $MgCl_2$. An approximate 10-fold and 5-fold reduction in IL-6 and IL-8 levels, respectively, was observed in NL20 cells treated with 300 μg/ml levofloxacin or 300 μg/ml levofloxacin formulated with $MgCl_2$. (FIGS. 4A and 4B). In addition, reductions in IL-6 and IL-8 levels were observed in HBE cells treated with 300 μg/ml levofloxacin or 300 μg/ml levofloxacin formulated with $MgCl_2$ (FIGS. 4C and 4D). Levofloxacin and levofloxacin formulated with $MgCl_2$ had similar activity in vitro.

Example 5

In Vitro Activity of Levofloxacin and Tobramycin

TNFα-induced NL20 cells and LPS-induced HBE135 cells were treated with 10-300 μg/ml levofloxacin, or tobramycin. No significant changes in cell viability in cytotoxicity assays were observed between any treatment (data not shown).

In NL20 cells treated with 10 ng/ml TNFα, an increase in IL-6 production from 3.4±0.2 μg/ml to 40.3±2.3 μg/ml was observed (FIG. 5A). IL-8 production increased from 3.3±0.2 μg/ml to 197.3±28.9 μg/ml (FIG. 5B). Incubation of NL20 cells with 5 μg/ml LPS did not produce significant increases in either IL-6 or IL-8 production (data not shown). The addition of 10 μg/ml or 30 μg/ml levofloxacin did not significantly change the level of IL-6 and IL-8 produced by NL20 cells. However, 100 μg/ml and 300 μg/ml levofloxacin resulted in 2- to 4-fold reductions in IL-6 levels, respectively ($p<0.005$) (FIG. 5A). Levels of IL-8 decreased by 50% and 60% in NL20 cells treated with 100 μg/ml and 300 μg/ml levofloxacin, respectively ($p<0.005$) (FIG. 5B). 10 μg/ml to 100 μg/ml tobramycin did not significantly affect production of IL-6 or IL-8 (FIGS. 5A and 5B). However, 300 mg/ml tobramycin produced an increase in IL-6 production (FIG. 5A). Thus, levofloxacin demonstrates an ability to reduce pro-inflammatory cytokine production in vitro in NL20 cells Incubation of HBE135 cells with 5 μg/ml LPS increased IL-6 production from 46.1±6.4 μg/ml to 86.3±6.4 μg/ml and IL-8 production from 280.7±54.9 μg/ml to 541.9±54.8 μg/ml. Incubation of HBE135 cells with 10 or 30 μg/ml levofloxacin and LPS cells did not significantly change IL-6 and IL-8 levels. However, 100 μg/ml and 300 μg/ml levofloxacin resulted in a 45% and 40% decrease in IL-6 levels, respectively (FIG. 6). Levels of IL-8 decreased by 30% and 20% in HBE135 cells treated with 100 μg/ml and 300 μg/ml levofloxacin, respectively (FIG. 6). Incubation of cells with 10 μg/ml, 30 μg/ml, or 100 μg/ml tobramycin did not affect the levels of IL-6, while 300 μg/ml of tobramycin increased levels of IL-6 by 30%. Treatment with 30 μg/ml to 300 μg/ml tobramycin increased IL-8 production by 20% to 30% ($p<0.05$).

These in vitro studies demonstrated that levofloxacin can induce a dose-related reduction in the production of the pro-inflammatory cytokines, IL-6 and IL-8, in cultured human lung epithelial cell lines. 300 μg/ml levofloxacin reduced levels of IL-6 by 4-fold and IL-8 by 2-fold ($p<0.05$); in contrast, tobramycin increased IL-6 levels by 50%, but had no effect on IL-8. These findings suggest that high concentrations of levofloxacin obtained in pulmonary tissues following treatment with aerosol levofloxacin formulated with $MgCl_2$ will provide antinflammatory benefits in patients with chronic pulmonary infections.

Example 6

In Vitro Activity of Levofloxacin in Human Monocytic Cells

The human monocyte cell line, THP-1 is an established in vitro model of human monocytic cells and is capable to secrete a greater variety of cytokines compared to NL20 and HBE135 cells. THP-1 cells were cultured in RPMI-1640 medium with 10% FBS, 0.05 mM 2-mecraptoethanol. THP-1 cells were seeded on 24-well tissue culture plates at $1\times10^6$ cells/ml in growth media without serum. The following day, 100 ng/ml LPS from *P. aeruginosa* and antibiotics were added and cells incubated for 24 hours before media collection to assess cytokine production. Quantification of IL-6, IL-8, IL-1β and TNFα production was performed as described above for NL20 cells.

Stimulation of THP-1 with 10 ng/ml of LPS increased IL-1β, TNFα, IL-6 and IL-8 levels by 60-, 200-, 30- and 600-fold, respectively (FIGS. 7A, 7B, 7C, and 7D). Co-incubation of LPS and at 100 μg/ml and 300 μg/ml levofloxacin resulted in a 40% and 70% decrease in IL-1β levels, respectively (FIG. 7A). 300 μg/ml levofloxacin increased TNFα production (FIG. 7B). Incubation with increased concentrations of levofloxacin caused dose-dependent decrease of IL-6 production, with 300 μg/ml levofloxacin reducing IL-6 levels by five-fold (FIG. 7C). Levels of IL-8 were significantly decreased by 100 μg/ml and 300 μg/ml levofloxacin (FIG. 7D).

Example 7

In Vitro Activity of Levofloxacin on IL-8 mRNA Expression

The human monocyte cell line, THP-1 is an established in vitro model of human monocytic cells and is capable to secrete a greater variety of cytokines compared to NL20 and HBE135 cells. IL-8 mRNA expression in NL20 monolayers was induced by treatment with 10 ng/ml TNFα. Levofloxacin was added simultaneously with TNFα. After 24 h incubation, the cell monolayer was washed with PBS, total cellular RNA was prepared and reverse transcription was performed using a human IL-8 specific primer and the "Cells-to-cDNA" kit from Ambion (Austin, Tex.). cDNA was subjected to real-time PCR analysis using PowerSYBR Green PCR master mix and a GeneAmp 5700 Instrument (Applied Biosystems; Warrington, UK). All data were normalized to the housekeeping gene β-actin. Stimulation of NL-20 cells with TNFα, produced a statistically significant ($p<0.005$) 20-fold increase in IL-8 mRNA levels (FIG. 8). This increase correlates with the increased levels of IL-8 protein induced by TNFα. Addition of 100 μg/ml and 300 μg/ml levofloxacin had no significant effect on the level of IL-8 mRNA expression (FIG. 4). These results suggest that levofloxacin reduces levels of the IL-8 secreted protein by modulating processes that include protein translation and/or protein secretion.

Example 8

In Vitro Activity of Levofloxacin on NFkB Activity

NFkB and AP-1 are important regulators in the transcriptional activity of some pro-inflammatory cytokines. This example relates to the effect of levofloxacin on the transcriptional regulatory activity of NFkB.

The human monocyte cell line, THP-1 is an established in vitro model of human monocytic cells and is capable to secrete a greater variety of cytokines compared to NL20 and HBE135 cells. Cells were seeded on 96-well plate at $3\times10^4$ cells/well and transfected the following day with a pMetLuc-NFkB reporter plasmid (Clontech) encoding a secreted luciferase protein under the control of a NFkB-regulated promoter. To normalize transfection efficiency, cells were cotransfected with a pSEAP-Control plasmid (Clontech) encoding a secreted alkaline phosphatase under the control of a strong constitutive promoter. 24 hours after transfection, media was replaced with fresh serum-free media containing 10 ng/ml TNF-α and levofloxacin. 8 hours after incubation, cell supernates were collected, and luciferase and alkaline phosphatase activities were measured using the "Ready-to-Glow Dual Secreted Reporter assay" (Clontech, Mountain View, Calif.). Cells transfected with the reporter plasmid encoding luciferase gene under control of NFkB transcription factor produced a low basal level of luciferase activity. Stimulation with TNFα, a known activator of the NFkB pathway, resulted in an almost 20-fold increase in promoter activity (FIG. 9). Addition of 100 μg/ml and 300 μg/ml levofloxacin did not produce a significant effect on the level of reporter gene activity. This suggests that levofloxacin did not affect TNFα-stimulated transcriptional activity of NFkB.

Example 9

In Vivo Anti-Inflammatory Activity of Levofloxacin Formulated with $MgCl_2$

Mice (n=4) were injected with 50 μg LPS by an intraperitoneal route. Thirty minutes after LPS treatment, mice were treated using a microspray aerosol device (PennCentury, Philadelphia) with 60 mg/kg saline control, levofloxacin formulated with $MgCl_2$, or tobramycin. Mice were sacrificed 6 hours after aerosolized treatment, and bronchoalveolar (BAL) fluid was collected by lavage with 1 ml saline. IL-6 and MIP-2 (murine homolog of human IL-8) levels were determined by ELISA.

Treatments with saline, levofloxacin formulated with $MgCl_2$, and tobramycin resulted in mean MIP-2 levels of 515 μg/ml, 233 μg/ml, and 502 μg/ml, respectively (FIG. 10A). Treatment with levofloxacin formulated with $MgCl_2$ resulted in more than a 2-fold reduction in MIP-2 levels relative to the saline control. Moreover, the reduction was significantly greater than both saline and tobramycin treated mice ($p<0.05$). A similar trend was observed in IL-6 levels (FIG. 10B). Treatment with levofloxacin produced IL-6 levels more than 2-fold lower than IL-6 levels in the saline control ($p<0.05$). Treatment with tobramycin resulted in an increase in IL-6 levels compared to the saline control. This in vivo data is consistent with the in vitro data of Example 5, where treatment with levofloxacin decreased levels of IL-6 and IL-8, while tobramycin had no significant effect on IL-8 levels and a trend towards increasing IL-6 levels.

This in vivo study shows that treatment with high concentrations of levofloxacin formulated with $MgCl_2$ can reduce pro-inflammatory cytokines that include IL-6 and IL-8. Accordingly, these findings suggest that in addition to potent antibacterial effects, high concentrations of levofloxacin may have anti-inflammatory benefits in patients susceptible to acute and chronic inflammations, for example patients with CF and COPD.

Example 10

Anti-Inflammatory Activity Of Levofloxacin Formulated with $MgCl_2$ in CF Patients CF patients having acute or chronic pulmonary inflammation are administered aerosol levofloxacin formulated with $MgCl_2$. After treatment, a reduction in the acute inflammation is observed. A reduction in the levels of pro-inflammatory cytokines is observed. A reduction in the levels of IL-1β, IL-6, and IL-8 in the lungs is observed. A reduction in the levels of IL-1β, IL-6, and IL-8 in the sputum and/or BAL is observed.

Example 11

Anti-Inflammatory Activity Of Levofloxacin Formulated with $MgCl_2$ in COPD Patients COPD patients having acute or chronic pulmonary inflammation are administered aerosol levofloxacin formulated with $MgCl_2$. After treatment, a reduction in the acute inflammation is observed. A reduction in the levels of pro-inflammatory cytokines is observed. A reduction in the levels of IL-1β, IL-6, and IL-8 in the lungs is observed. A reduction in the levels of IL-1β, IL-6, and IL-8 in the sputum and/or BAL is observed.

Example 12

Anti-Inflammatory Activity of Levofloxacin Formulated with $MgCl_2$ in Chronic Bronchitis Patients Chronic bronchitis patients having acute or chronic pulmonary inflammation are administered aerosol levofloxacin formulated with $MgCl_2$. After treatment, a reduction in the acute inflammation is observed. A reduction in the levels of pro-inflammatory cytokines is observed. A reduction in the levels of IL-1β, IL-6, and IL-8 in the lungs is observed. A reduction in the levels of IL-1β, IL-6, and IL-8 in the sputum and/or BAL is observed.

Example 13

Anti-Inflammatory Activity Of Levofloxacin Formulated with $MgCl_2$ in Bronchiectasis Patients Bronchiectasis patients having acute or chronic pulmonary inflammation are administered aerosol levofloxacin formulated with MgCl$_2$. After treatment, a reduction in the acute inflammation is observed. A reduction in the levels of pro-inflammatory cytokines is observed. A reduction in the levels of IL-1β, IL-6, and IL-8 in the lungs is observed. A reduction in the levels of IL-1β, IL-6, and IL-8 in the sputum and/or BAL is observed.

Example 14

Anti-Inflammatory Activity Of Levofloxacin Formulated with MgCl$_2$ in Non-CF Bronchiectasis Patients Non-CF bronchiectasis patients having acute or chronic pulmonary inflammation are administered aerosol levofloxacin formulated with MgCl$_2$. After treatment, a reduction in the acute inflammation is observed. A reduction in the levels of pro-inflammatory cytokines is observed. A reduction in the levels of IL-1β, IL-6, and IL-8 in the lungs is observed. A reduction in the levels of IL-1β, IL-6, and IL-8 in the sputum and/or BAL is observed.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for treating a pulmonary inflammation in the absence of a pulmonary bacterial infection in a subject comprising administering to said subject in need thereof an aerosol of a solution comprising levofloxacin or ofloxacin and a divalent or trivalent cation, wherein the solution comprises a divalent or trivalent cation concentration from about 150 mM to about 250 mM, and a levofloxacin or ofloxacin concentration from about 90 mg/ml to about 125 mg/ml.

2. The method of claim 1, wherein the subject has a disorder selected from the group consisting of asthma, cystic fibrosis (CF), pulmonary fibrosis, chronic bronchitis (CB), bronchiectasis, chronic granulomatous disease, sinusitis, chronic obstructive pulmonary disease (COPD), and pneumonia.

3. The method of claim 1, wherein the solution consists essentially of levofloxacin or ofloxacin and the divalent or trivalent cation.

4. The method of claim 1, wherein the solution comprises chloride.

5. The method of claim 1, wherein the solution comprises no lactose.

6. The method of claim 1, wherein the solution has an osmolality from about 300 mOsmol/kg to about 500 mOsmol/kg, and a pH from about 5 to about 8.

7. The method of claim 1, wherein the solution has an osmolality from about 350 mOsmol/kg to about 425 mOsmol/kg, and a pH from about 5 to about 6.5.

8. The method of claim 1, wherein the solution has a pH from about 5.5 to about 6.5.

9. The method of claim 1, wherein the divalent or trivalent cation is selected from magnesium, calcium, zinc, copper, aluminum, and iron.

10. The method of claim 1, wherein the solution comprises magnesium chloride.

11. The method of claim 1, wherein the solution has a levofloxacin or ofloxacin concentration from about 90 mg/ml to about 110 mg/ml, a magnesium chloride concentration between about 175 mM to about 225 mM, a pH between about 5 to about 7; an osmolarity of from about 300 mOsmol/kg to about 500 mOsmol/kg, and lacks lactose.

12. The method of claim 1, wherein the aerosol comprises a mass median aerodynamic diameter from about 2 microns to about 5 microns with a geometric standard deviation less than or equal to about 2.5 microns.

13. The method of claim 1, wherein the aerosol comprises a mass median aerodynamic diameter from about 2.5 microns to about 4.5 microns with a geometric standard deviation less than or equal to about 1.8 microns.

14. The method of claim 1, wherein the aerosol comprises a mass median aerodynamic diameter from about 2.8 microns to about 4.3 microns with a geometric standard deviation less than or equal to about 2 microns.

15. The method of claim 1, comprising producing the aerosol with a vibrating mesh nebulizer.

16. The method of claim 15, wherein the vibrating mesh nebulizer is a PARI E-FLOW® nebulizer.

17. The method of claim 1, wherein at least about 20 mg of levofloxacin or ofloxacin is administered to the lung.

18. The method of claim 1, wherein at least about 100 mg of levofloxacin or ofloxacin is administered to the lung.

19. The method of claim 1, wherein at least about 125 mg of levofloxacin or ofloxacin is administered to the lung.

20. The method of claim 1, wherein at least about 150 mg of levofloxacin or ofloxacin is administered to the lung.

21. The method of claim 1, wherein the aerosol is administered to the lung in less than about 10 minutes.

22. The method of claim 1, wherein the aerosol is administered to the lung in less than about 5 minutes.

23. The method of claim 1, wherein the aerosol is administered to the lung in less than about 3 minutes.

24. The method of claim 1, wherein the aerosol is administered to the lung in less than about 2 minutes.

25. The method of claim 1, comprising administering the aerosol once daily.

26. The method of claim 1, comprising administering the aerosol twice daily.

27. The method of claim 1, further comprising co-administering an additional active agent selected from the group consisting of anti-inflammatory agent, antibiotic, bronchodilator, anticholinergic, glucocorticoid, eicosanoid inhibitor, and combinations thereof.

28. The method of claim 27, wherein co-administering comprises inhaling the additional active agent.

29. The method of claim 27, wherein the antibiotic is selected from the group consisting of tobramycin, aztreonam, ciprofloxacin, azithromycin, erythromycin tetracycline, quinupristin, linezolid, vancomycin, and chloramphenicol, colisitin and combinations thereof.

30. The method of claim 27, wherein the bronchodilator is selected from the group consisting of salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast, and combinations thereof.

31. The method of claim 27, wherein the anticholinergic is selected from the group consisting of ipratropium, tiotropium, and combinations thereof.

32. The method of claim 27, wherein the glucocorticoid is selected from the group consisting of prednisone, fluticasone, budesonide, mometasone, ciclesonide, beclomethasone, and combinations thereof.

33. The method of claim 27, wherein the eicosanoid inhibitor is selected from the group consisting of montelukast, pranlukast, zafirlukast, zileuton, ramatroban, seratrodast, and combinations thereof.

34. A method for treating a pulmonary inflammation in the absence of a pulmonary bacterial infection in a subject, wherein the pulmonary inflammation is induced by one or more pro-inflammatory cytokines, said method comprising administering to said subject in need thereof an aerosol of a solution comprising levofloxacin or ofloxacin and a divalent or trivalent cation to achieve a reduction in the pulmonary concentration of said cytokine by at least 10%, wherein the solution comprises a divalent or trivalent cation concentration from about 150 mM to about 250 mM, and a levofloxacin or ofloxacin concentration from about 90 mg/ml to about 125 mg/ml.

35. The method of claim 34, wherein the pulmonary concentration of said cytokine is reduced by at least 20%.

36. The method of claim 34, wherein the pulmonary concentration of said cytokine is reduced by at least 40%.

37. The method of claim 34, wherein the pulmonary concentration of said cytokine is reduced by at least 60%.

38. The method of claim 34, wherein the pulmonary concentration of said cytokine is reduced by at least 80%.

39. A method for treating a pulmonary inflammation in the absence of a pulmonary bacterial infection in a subject comprising administering to said subject in need thereof an aerosol of a solution comprising levofloxacin or ofloxacin and a divalent or trivalent cation to achieve a reduction in the pulmonary concentration of one or more pro-inflammatory cytokines selected from IL-1β, IL-6 and IL-8, whereby the pulmonary inflammation is reduced or suppressed, wherein the solution comprises a divalent or trivalent cation concentration from about 150 mM to about 250 mM, and a levofloxacin or ofloxacin concentration from about 90 mg/ml to about 125 mg/ml.

40. The method of claim 39, wherein the cytokine comprises IL-1β.

41. The method of claim 39, wherein the cytokine comprises IL-6.

42. The method of claim 39, wherein the cytokine comprises IL-8.

43. A method for treating a pulmonary inflammation in the absence of a pulmonary bacterial infection in a subject, wherein the pulmonary inflammation is induced by one or more mediators selected from TNFα and LPS, said method comprising administering to said subject in need thereof an aerosol of a solution comprising levofloxacin or ofloxacin and a divalent or trivalent cation, wherein the solution comprises a divalent or trivalent cation concentration from about 150 mM to about 250 mM, and a levofloxacin or ofloxacin concentration from about 90 mg/ml to about 125 mg/ml.

44. A method for reducing the pulmonary concentration of one or more pro-inflammatory cytokine in the absence of a pulmonary bacterial infection in a subject, said method comprising administering to said subject in need thereof an aerosol of a solution comprising levofloxacin or ofloxacin and a divalent or trivalent cation, wherein the solution comprises a divalent or trivalent cation concentration from about 150 mM to about 250 mM, and a levofloxacin or ofloxacin concentration from about 90 mg/ml to about 125 mg/ml.

45. The method of claim 44, wherein the cytokine comprises IL-1β.

46. The method of claim 44, wherein the cytokine comprises IL-6.

47. The method of claim 44, wherein the cytokine comprises IL-8.

* * * * *

UNITED STATES PATENT AND TRADEMARK OFFICE
CERTIFICATE OF CORRECTION

| | |
|---|---|
| PATENT NO. | : 8,629,139 B2 |
| APPLICATION NO. | : 12/574666 |
| DATED | : January 14, 2014 |
| INVENTOR(S) | : Michael N. Dudley et al. |

It is certified that error appears in the above-identified patent and that said Letters Patent is hereby corrected as shown below:

On the Title Page

At Item 56, Page 3, Column 1, Line 65, Under Other Publications, change "Anti-inflmmatory" to --Anti-inflammatory--.

At Item 56, Page 3, Column 2, Line 24, Under Other Publications, change "idan" to --indan--.

At Item 56, Page 3, Column 2, Line 25, Under Other Publications, change "indacterol" to --indacaterol--.

At Item 56, Page 3, Column 2, Line 37, Under Other Publications, change "Aeruginos" to --Aeruginosa--.

At Item 56, Page 4, Column 1, Line 42, Under Other Publications, change "sposbe" to --sposobe--.

At Item 56, Page 4, Column 1, Line 44, Under Other Publications, change "miditsinskoi" to --meditsinskoi--.

At Item 56, Page 4, Column 1, Line 45, Under Other Publications, change "promyshelennosti" to --promyshiennosti--.

At Item 56, Page 5, Column 1, Line 52, Under Other Publications, change "thereapeutic" to --therapeutic--.

At Item 56, Page 6, Column 2, Line 24, Under Other Publications, change "Azitromycin" to --Azithromycin--.

At Item 56, Page 6, Column 2, Line 41, Under Other Publications, change "ano" to --and--.

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,629,139 B2

At Item 56, Page 6, Column 2, Line 48, Under Other Publications, change "Inter'I" to --Inter'l--.

At Item 56, Page 6, Column 2, Line 69, Under Other Publications, change "rhinoviral" to --rhinovirus--.

In the Specification

At Column 4, Line 15, change "lipopolysacchararide" to --lipopolysaccharide--.

At Column 6, Line 47, change "naphtoic" to --napthoic--.

At Column 6, Line 52, change "lactobioic" to --lactobionic--.

At Column 7, Line 1, change "dodecylsufuric" to --dodecylsulfonic--.

At Column 8, Line 9, change "alveoial" to --alveoli--.

At Column 8, Line 43, change "colisitin" to --colistin--.

At Column 8, Line 52, change "levosalbuterol" to --levosalbutamol--.

At Column 9, Line 4, change "simavastatin" to --simvastatin--.

At Column 9, Line 6, change "non-steriodal" to --non-steroidal--.

At Column 9, Lines 27-28, change "nonsteriodal" to --nonsteroidal--.

At Column 10, Line 49, change "crosscarmellose" to --croscarmellose--.

At Column 10, Line 53, change "cyclodextrine" to --cyclodextrin--.

At Column 11, Lines 47-48, change "crosscarmellose" to --croscarmellose--.

At Column 15, Line 63, change "cells" to --cells.--.

At Column 16, Line 21, change "antinflammatory" to --anti-inflammatory--.

At Column 16, Line 33, change "2-mercraptoethanol" to --2-mercaptoethanol--.

In the Claims

At Column 21, Line 47, change "collsitin" to --colistin--.

At Column 21, Lines 49-50, change "levosalbuterol" to --levosalbutamol--.